United States Patent
Narasimharao et al.

(10) Patent No.: US 11,161,093 B1
(45) Date of Patent: Nov. 2, 2021

(54) GOLD-DECORATED MAGNESIUM SILICATE CATALYST FOR PRODUCING LIGHT OLEFINS

(71) Applicant: King Abdulaziz University, Jeddah (SA)

(72) Inventors: Katabathini Narasimharao, Jeddah (SA); Sulaiman Nasir Basahel, Jeddah (SA); Abdulmohsen Al Shehri, Jeddah (SA); Fawaz Saleh Al-Sultan, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/232,943

(22) Filed: Apr. 16, 2021

(51) Int. Cl.
| | |
|---|---|
| *B01J 21/16* | (2006.01) |
| *B01J 23/52* | (2006.01) |
| *B01J 35/02* | (2006.01) |
| *B01J 35/10* | (2006.01) |
| *B01J 21/14* | (2006.01) |
| *B01J 37/03* | (2006.01) |
| *C07C 4/06* | (2006.01) |
| *B01J 37/08* | (2006.01) |
| *B01J 37/04* | (2006.01) |
| *B82Y 30/00* | (2011.01) |
| *B82Y 40/00* | (2011.01) |

(52) U.S. Cl.
CPC .............. *B01J 21/14* (2013.01); *B01J 23/52* (2013.01); *B01J 35/1019* (2013.01); *B01J 35/1038* (2013.01); *B01J 35/1057* (2013.01); *B01J 35/1061* (2013.01); *B01J 37/031* (2013.01); *B01J 37/04* (2013.01); *B01J 37/082* (2013.01); *C07C 4/06* (2013.01); *B82Y 30/00* (2013.01); *B82Y 40/00* (2013.01)

(58) Field of Classification Search
CPC ........................................................ B01J 23/16
See application file for complete search history.

(56) References Cited

U.S. PATENT DOCUMENTS

| | | |
|---|---|---|
| 4,732,747 A | 3/1988 | Garces |
| 8,350,108 B2 | 1/2013 | Cortright et al. |
| 2004/0068148 A1 | 4/2004 | Allison et al. |

(Continued)

FOREIGN PATENT DOCUMENTS

| | | | |
|---|---|---|---|
| CN | 1177644 C | 12/2004 | |
| EP | 2712673 A1 * | 4/2014 | ............... C07C 1/20 |

(Continued)

OTHER PUBLICATIONS

Shylesh (From Sugars to Wheels: The Conversion of Ethanol to 1,3-Butadiene over Metal-Promoted Magnesia-Silicate Catalysts, ChemSusChem, 2016, 9 )-supplemental information.*

(Continued)

*Primary Examiner* — Jun Li
(74) *Attorney, Agent, or Firm* — Oblon, McClelland, Maier & Neustadt, L.L.P.

(57) ABSTRACT

A nanomaterial catalyst comprising a partially crystalline porous magnesium silicate support and gold nanoparticles, the catalyst being useful for oxidative cracking of hydrocarbons, specifically the production of light olefins from propane. Methods of producing the nanomaterial catalyst as well as a method of oxidative cracking of a hydrocarbon to produce light olefins are provided.

7 Claims, 8 Drawing Sheets

(56) References Cited

U.S. PATENT DOCUMENTS

| | | | | |
|---|---|---|---|---|
| 2009/0011925 A1* | 1/2009 | Felix | ............... | B01J 23/80 502/60 |
| 2009/0092836 A1* | 4/2009 | Geckeler | ............... | B01J 23/52 428/403 |
| 2015/0151279 A1* | 6/2015 | Haruta | ............... | B01J 37/0211 502/304 |

FOREIGN PATENT DOCUMENTS

| | | |
|---|---|---|
| JP | 2015168644 A * | 9/2015 |
| KR | 10-0669000 | 1/2007 |
| WO | 2005/056181 A1 | 6/2005 |
| WO | WO-2014061917 A1 * | 4/2014 ......... B01J 29/0316 |

OTHER PUBLICATIONS

Machine translation of Nakatani (JP2015-168644A), publication date Sep. 28, 2015.*
Machine translation of Haufe (EP2712673A1), Apr. 2, 2014.*
Machine translation of Chae (WO2014/016917A1), Apr. 24, 2014.*

Jones, et al. ; Sol-Gel Synthesis and Characterization of Magnesium Silicate Thin Films ; Chem. Mater. 1997, 9 ; pp. 2567-2576 ; 10 Pages.
Brew, et al. ; Synthesis and characterisation of magnesium silicate hydrate gels ; Cement and Concrete Research 35 (2005) ; pp. 85-98 ; Jun. 4, 2004 ; 14 Pages.
Janssens, et al. ; Ternary Ag/MgO—SiO2 Catalysts for the Conversion of Ethanol into Butadiene ; ChemSusChem 2015, 8 ; pp. 994-1008; 15 Pages.
Chung, et al. ; Role of Magnesium Silicates in Wet-Kneaded Silica-Magnesia Catalysts for the Lebedev Ethanol-to-Butadiene Process ; American Chemical Society Catal. 2016, 6 ; pp. 4034-4045 ; 12 Pages.
Ghods, et al. ; Ni Catalysts Supported on Mesoporous Nanocrystalline Magnesium Silicate in Dry and Steam Reforming Reactions ; Chem. Eng. Technol. 2017, 40, No. 4 ; pp. 760-768 ; Feb. 10, 2017 ; 9 Pages.
Shylesh, et al. ; From Sugars to Wheels: The Conversion of Ethanol to 1,3-Butadiene over Metal-Promoted Magnesia-Silicate Catalysts ; ChemSusChem 2016, 9 ; pp. 1462-1472 ; 11 Pages.
Mashayekhi, et al. ; Selective oxidation of hydrocarbons on supported Au catalysts ; Catalysis Today, vol. 238 ; pp. 74-79 ; Dec. 2014 ; Abstract Only ; 3 Pages.

* cited by examiner

GOLD-DECORATED MAGNESIUM SILICATE CATALYST FOR PRODUCING LIGHT OLEFINS

BACKGROUND OF THE INVENTION

Field of the Invention

The present disclosure relates to a gold-decorated magnesium silicate nanomaterial catalyst and a method for producing light olefins by oxidative cracking using the same.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The demand for light olefins such as ethylene and propylene has increased immensely, as the present industrial production of light olefins is not adequate [F. Cavani, N. Ballarini, A. Cericola, Catal. Today 127 (2007) 113-131]. The existing industrial processes producing light olefins, along with methane and aromatics, use catalytic or steam cracking of naphtha and natural gas [Sanfilippo D, Miracca. Catal. Today 111 (2006) 133-139]. Some other petrochemical sectors are utilizing fluid catalytic cracking of vacuum residue for olefins production. Although the established processes are thoroughly studied and commercialized, these processes still suffer from several disadvantages [Pyrolysis Corcoran WH. Theory and industrial practice. New York: Academic Press. 1983. p. 47-68]. Researchers have also investigated olefin production by dehydrogenation of short chain alkanes, however this process also suffers from shortcomings such as being endothermic in nature, coke deposition and short catalyst lifespan [M. Huff, L. D. Schmidt, J. Catal. 194 (1994) 127-141]. A promising route to olefin production is catalytic oxidative dehydrogenation, which was emerged to overcome the disadvantages of non-catalytic or non-oxidative dehydrogenation processes [V. R. Choudhary, S. A. R. Mulla, Appl. Energy 68 (2001) 377-386; and S. Cimino, F. Donsi, G. Russo, D. Sanfilippo, Catal. Today 157 (2010) 310-314]. Catalytic oxidative cracking has emerged as a potential alternative to other existing processes for selective olefin production. [L. Basini, S. Cimino, A. Guarinoni, G. Russo, V. Arca, Chem. Eng. J. 207-208 (2012) 473-480].

Catalytic oxidative cracking is inherently exothermic in nature, an advantage over dehydrogenation processes. The heat produced as well as the use of oxygen as a reactant assist to minimize coke formation. Light olefin production methods are typically energy-intensive processes and yield a complex mixture of products. Catalytic oxidative cracking may both lower the reaction temperatures required and increase product selectivity, both of which are highly dependent upon the properties of the catalyst [O. V. Buyevskaya, D. Mialler, I. Pitsch, M. Baems, Stud. Sur. Sci Catal. 119 (1998) 671-676]. Light olefin production through the catalytic cracking of hydrocarbons using aluminum silicates (zeolites) was first studied by Pop et al. These researchers used a bifunctional Ag/Cu/Co-mordenite-$Al_2O_3$ catalyst in the temperature range of 600-750° C. to produce ethylene and propylene in yields of 8-41% and 11-17%, respectively [U.S. Pat. No. 4,172,816]. The studies on zeolite-based catalysts typically report low ethylene yields (15-27%), but high propylene (15-50%) and aromatics (11-34%) yields at low reaction temperatures compared with the conventional steam cracking process.

Wakui et al. investigated the effect of alkaline earth metal (Mg, Ca, Sr and Ba) modification on the performance of H-ZSM-5 for the catalytic cracking of n-butane [K. Wakui, K. Sato, G. Sawada, K. Matano, T. Hayakawa, Y. Yoshimura, K. Murata, F. Mizukami, Catal. Lett. 84 (2002) 259-264]. Lu et al. observed very high catalytic activity and selectivity in the catalytic cracking of iso-butane over Fe/H-ZSM-5 (Si/Al=32) and Cr/H-ZSM-5 (Si/Al=32) catalysts at 625° C. [J. Lu, Z. Zhao, C. Xu, P. Zhang, A. Duan, Catal. Commun. 7 (2006) 199-203]. Later, Yoshimura et al. investigated the oxidative cracking process over solid acid and base catalysts for oxidative and non-oxidative cracking and achieved promising results over phosphorous modified $La_2O_3$/ZSM-5 catalyst. The developed catalyst offered high yields of olefins at 600° C. compared to steam cracking processes operated at 820° C. [Y. Yoshimura, N. Kijima, T. Hayakawa, K. Murataa, K. Suzuki, F. Mizukami, K. Matano, T. Konishi, T. Oikawa, M. Saito, T. Shiojima, K. Shiozawa, K. Wakui, G. Sawada, K. Sato, S. Matsuo, N. Yamaoka, Catal. Surv. Jon. 4 (2000) 157-167]. Feng et al. utilized fluorinated H-ZSM-5 catalyst as an efficient catalyst for the catalytic cracking of naphtha to light olefins [X. Feng, G. Jiang, Z. Zhao, L. Wang, X. Li, A. Duan, J. Liu, C. Xu, J. Gao, Energy Fuels 24 (2010) 4111-4115]. Altwasser et al. studied the influence of pore size of zeolites and spatial constraints over the reaction mechanisms of the catalytic cracking of n-octane [S. Altwasser, C. Welker, Y. Traa, J. Weitkamp, Microporous Mesoporous Mater. 83 (2005) 345-356]. Wei et al. utilized alkali ion-exchanged H-ZSM-5 zeolites to improve the yield of light olefins in catalytic cracking of n-hexane [Y. Wei, F. Chang, Y. He, S. Meng, Y. Yang, Y. Qi, Z. Liu, Recent Prog. Mesostruct. Mater. (2007) 539-542]. Zhu et. al. investigated the influence of Si/Al ratio of ZSM-5 zeolites in catalytic cracking and found that the yields of propylene and ethylene were increased with increase of Si/Al ratio [X. Zhu, S. Liu, Y. Song, L. Xu, Appl. Catal. A: Gen. 288 (2005) 134-142]. It was also reported that lowering the acidity of P/H-ZSM-5 catalyst was used as a tool to enhance light olefin production, as the introduction of P in H-ZSM-5 resulted in an increase in the selectivity for olefins in the catalytic cracking of n-decane [T. Blasco, A. Corma, J. Martnez-Triguero, J. Catal. 237 (2006) 267-277; and Y. Wei, Z. Liu, G. Wang, Y. Qi, L. Xu, P. Xie, Y. He, Stud. Surf. Sci. Catal. 158 (2005) 1223-1230].

Magnesium silicates are low cost, stable, and safe materials; they are widely used as catalysts, inorganic phosphors, bio-nanocomposites, adsorption and separation processes [A. Krysztafkiewicz, L. K. Lipska, F. Ciesielczyk, T. Jesionowski, Advanced Powder Technol., 15, (2004) 549-565]. Application potential of non-zeolite silicates to a significant extent reflects their physicochemical properties. It is known that the magnesium silicates are well used materials for gas purification, oxidation, methanization and various hydrogenation reactions. In many cases, the magnesium silicate material acts as a pure support onto which the active metal (Pt, Ni, Cu, Fe or Co) component can be dispersed [D. R. M. Brew, F. P. Glasser, Cem. Concr. Res. 35 (2005) 85-98].

For example, Corma et al. studied a magnesium silicate supported vanadium catalyst for the oxidative dehydrogenation of propane to produce olefins [A. Corma, J. M. LópezNieto, N. Paredes, M. Perez, Appl. Catal. A: Gen. 97 (1993) 159-175]. Allison et al. described development of catalyst that comprises a Group VIII metal present at 0.005 and 0.1 wt. % and magnesium silicate for oxidative dehydrogenation of propane at low temperatures [US patent publication 20040068148A1]. Haruta, et al. developed a catalyst for partial oxidation of hydrocarbons, where the catalyst comprises gold nanoparticles supported by a titanium containing silicate [WIPO patent publication WO2005056181A1]. Janssens et. al. prepared Ag supported over MgO—$SiO_2$ catalysts by an impregnation method and the obtained catalysts were used for conversion of ethanol into butadiene [W. Janssens, E. V. Makshina, P. Vanelderen, F. De Clippel, K. Houthoofd, S. Kerkhofs, J. A. Martens, P. A. Jacobs, B. F. Sels, ChemSusChem. 8 (2015) 994-1008].

SUMMARY OF THE INVENTION

The present disclosure relates to a nanomaterial catalyst, comprising a partially crystalline porous magnesium silicate support which is substantially free of titanium and aluminum, and gold nanoparticles dispersed on the partially crystalline porous magnesium silicate support, wherein the nanomaterial catalyst is substantially free of Group VIII metals.

In some embodiments, the partially crystalline porous magnesium silicate support has a Mg to Si molar ratio of 1:1 to 5:1.

In some embodiments, the partially crystalline porous magnesium silicate support is a single crystalline phase by PXRD.

In some embodiments, partially crystalline porous magnesium silicate support has an average crystallite size of 5 to 50 nm by PXRD.

In some embodiments, the gold nanoparticles are present in an amount of 0.1 to 5 wt %, based on a total weight of nanomaterial catalyst.

In some embodiments, the gold nanoparticles have an average particle size of 5 to 100 nm.

In some embodiments, the nanomaterial catalyst has a surface area of 300 to 500 $m^2/g$, an average pore size of 1 to 25 nm, and a pore volume of 0.225 to 0.375 $cm^3/g$.

In some embodiments, the nanomaterial catalyst has an acidity of 7.5 to 30 mmol/g.

In some embodiments, the nanomaterial catalyst consists of the partially crystalline porous magnesium silicate support having a Mg to Si molar ratio of 1:1 to 5:1 and the gold nanoparticles having an average particle size of 5 to 100 nm dispersed on the partially crystalline porous magnesium silicate support, wherein the nanomaterial catalyst has a surface area of 300 to 500 $m^2/g$, a pore volume of 0.225 to 0.375 $cm^3/g$, and an acidity of 7.5 to 30 mmol/g.

The present disclosure also relates to a method for making the nanomaterial catalyst, the method comprising reacting a magnesium salt, colloidal silica, and a first solvent under solvothermal conditions at 120 to 200° C. for 2 to 24 hours produce a first precipitate, calcining the first precipitate at 250 to 750° C. to produce the partially crystalline porous magnesium silicate support, adding a gold precursor to a dispersion comprising the partially crystalline porous magnesium silicate support in a second solvent to produce a reduction mixture, heating the reduction mixture to 70 to 100° C. for 60 to 360 minutes to produce a second precipitate, and calcining the second precipitate at 250 to 750° C. to produce the nanomaterial catalyst.

In some embodiments, the magnesium salt is magnesium nitrate and the gold precursor is gold (III) chloride.

In some embodiments, the first solvent is water and the second solvent is a mixture of water and ethanol having a water-to-ethanol volumetric ratio of 3:1 to 1:3.

In some embodiments, the adding comprises injection of a gold solution comprising the gold precursor in a third solvent into the dispersion at a temperature of 70 to 100° C.

The current disclosure also relates to a method for making the nanomaterial catalyst, the method comprising mixing a magnesium salt, a water-soluble silicate source, a gold salt, and a solvent to form a precursor mixture, adjusting the pH of the precursor mixture to a pH>7 to form an adjusted reaction mixture, and reacting the adjusted reaction mixture under solvothermal conditions at 160 to 200° C. for 12 to 90 hours to produce the nanomaterial catalyst.

In some embodiments, the magnesium salt is magnesium nitrate, the gold salt is gold (III) chloride, and the water-soluble silicate source is sodium metasilicate.

In some embodiments, the solvent is a mixture of water and water and an alcohol selected from the group consisting of ethanol and 1-propanol, the mixture having a water-to-alcohol volumetric ratio of 1:3 to 1:1.

The present disclosure also relates to a method of oxidative cracking of a hydrocarbon having 3 to 6 carbon atoms, the method comprising contacting at a temperature of 650° C. or lower the nanomaterial catalyst with a gas mixture comprising 5 to 20 vol % of the hydrocarbon, 5 to 20 vol % oxygen, and 60 to 90 vol % of a carrier gas, wherein the contacting produces a light olefin.

In some embodiments, the hydrocarbon is propane.

In some embodiments, the method has a percentage conversion of the hydrocarbon of greater than 60%, based on a total amount of the hydrocarbon contacted with the nanomaterial catalyst.

In some embodiments, the method has a selectivity for the light olefin of greater than 65%, based on a total conversion of the hydrocarbon.

BRIEF DESCRIPTION OF THE DRAWINGS

FIG. 3A is for MgSil, FIG. 3B is for 0.5Au/MgSil, FIG. 3C is for 1.0Au/MgSil, FIG. 3D is for 1.5Au/MgSil, and FIG. 3E is for 2.0Au/MgSil;

FIG. 5A is for MgSil, FIG. 5B is for 0.5Au/MgSil, FIG. 5C is for 1.0Au/MgSil, FIG. 5D is for 1.5Au/MgSil, and FIG. 5E is for 2.0Au/MgSil;

FIG. 6A is for MgSil, FIG. 6B is for 0.5Au/MgSil, FIG. 6C is for 1.0Au/MgSil, FIG. 6D is for 1.5Au/MgSil, and FIG. 6E is for 2.0Au/MgSil;

FIG. 7A is the Mg2p spectrum for MgSil, FIG. 7B is the Si2p spectrum for MgSil, FIG. 7C is the O1s spectrum for MgSil, FIG. 7D is the Mg2p spectrum for 0.5Au/MgSil, FIG. 7E is the Si2p spectrum for 0.5Au/MgSil, FIG. 7F is the Au4f spectrum for 0.5Au/MgSil, FIG. 7G is the O1s spectrum for 0.5Au/MgSil, FIG. 7H is the Mg2p spectrum for 1.5Au/MgSil, FIG. 7I is the Si2p spectrum for 1.5Au/MgSil, FIG. 7J is the Au4f spectrum for 1.5Au/MgSil, and FIG. 7K is the O1s spectrum for 1.5Au/MgSil;

FIG. 8A is for MgSil, FIG. 8B is for 0.5Au/MgSil, FIG. 8C is for 1.0Au/MgSil, FIG. 8D is for 1.5Au/MgSil, and FIG. 8E is for 2.0Au/MgSil;

FIG. 9A is for MgSil, FIG. 9B is for 0.5Au/MgSil, FIG. 9C is for 1.0Au/MgSil, FIG. 9D is for 1.5Au/MgSil, and FIG. 9E is for 2.0Au/MgSil;

FIG. 10A is for MgSil, FIG. 10B is for 0.5Au/MgSil, FIG. 10C is for 1.0Au/MgSil, FIG. 10D is for 1.5Au/MgSil, and FIG. 10E is for 2.0Au/MgSil;

FIG. 11A is n-propane conversion and FIG. 11B is olefins selectivity;

FIG. 12A is conversion of n-propane and FIG. 12B is selectivity to olefins;

FIG. 13A is for MgSil and FIG. 13B is for 1.5Au/MgSil; FIG. 14A is for conversion of n-propane and FIG. 14B is for selectivity to olefins.

DETAILED DESCRIPTION OF THE INVENTION

Figure 1:
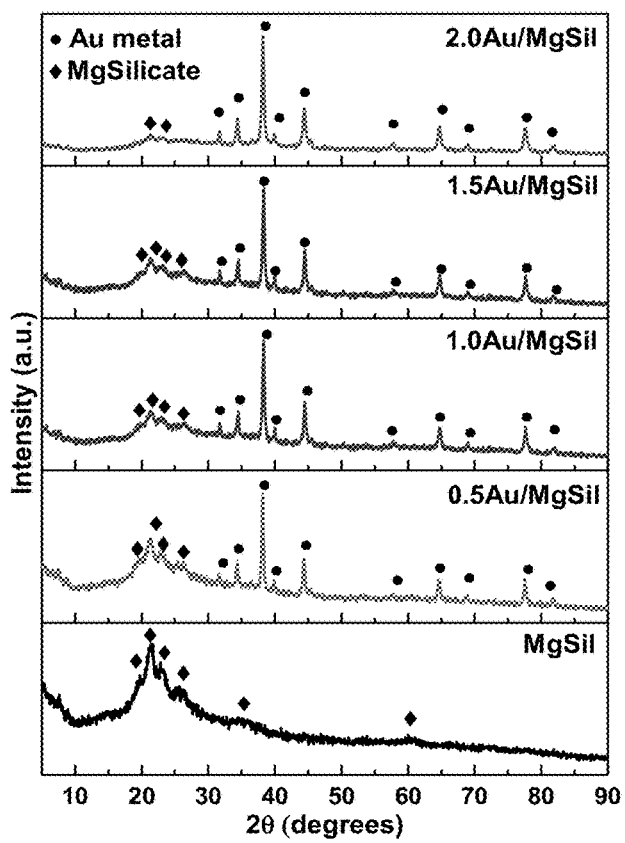
FIG. 1 shows powder XRD patterns of Au/MgSil samples.
Figure 2:
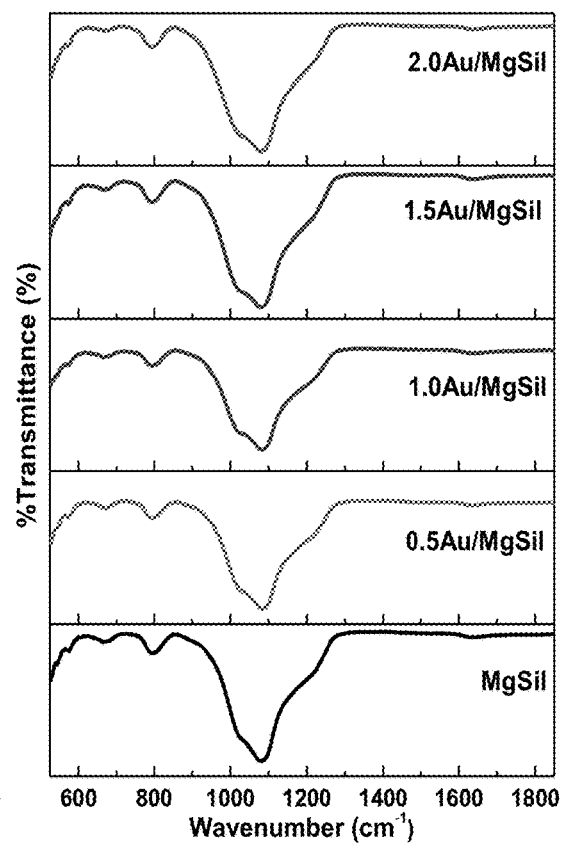
FIG. 2 shows FTIR spectra of Au/MgSil samples.
Figure 3A:
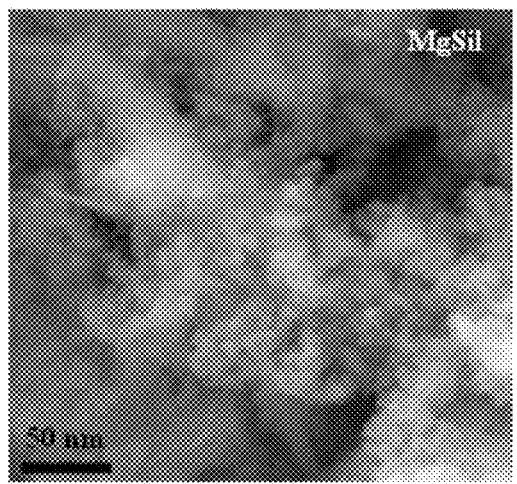
FIG. 3A-3E are SEM images of Au/MgSil samples where
Figure 3B:
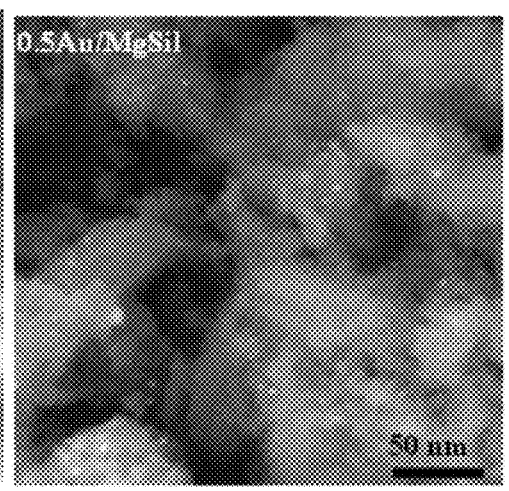
Figure 3C:
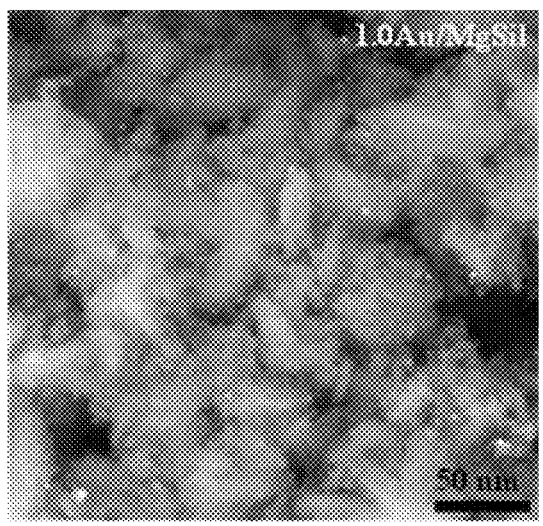
Figure 3D:
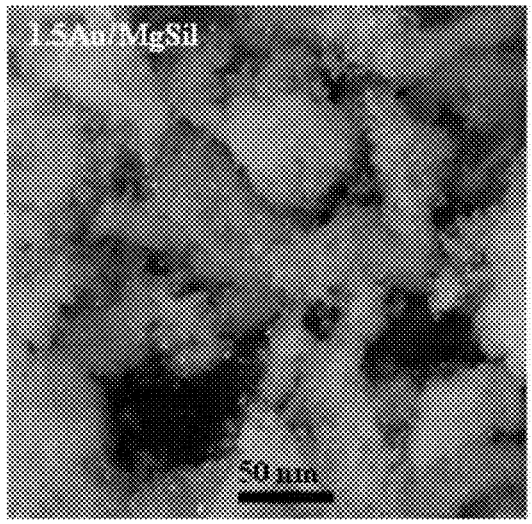
Figure 3E:
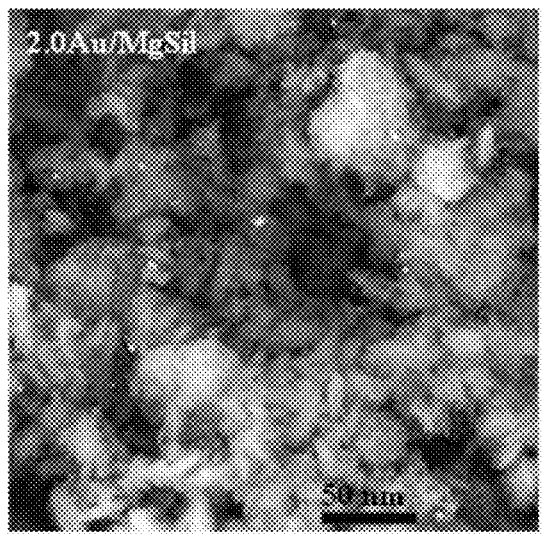

In the following description, it is understood that other embodiments may be utilized and structural and operational changes may be made without departure from the scope of the present embodiments disclosed herein.

Definitions

As used herein, the words "a" and "an" and the like carry the meaning of "one or more."

As used herein, the terms "optional" or "optionally" means that the subsequently described event(s) can or cannot occur or the subsequently described component(s) may or may not be present (e.g., 0 wt. %).

The present disclosure is intended to include all hydration states of a given compound or formula, unless otherwise noted or when heating a material. For example, magnesium nitrate, Mg(NO$_3$)$_2$, includes anhydrous Mg(NO$_3$)$_2$, Mg(NO$_3$)$_2$·6H$_2$O, and any other hydrated forms or mixtures.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium. Isotopes of carbon include $^{13}$C and $^{14}$C. Isotopes of nitrogen include $^{14}$N and $^{15}$N. Isotopes of oxygen include $^{16}$O, $^{17}$O, and $^{18}$O. Isotopes of silicon include $^{28}$Si, $^{29}$Si, and $^{30}$Si. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, even more preferably less than about 0.01 wt %, even more preferably less than about 0.001 wt %, yet even more preferably 0 wt. %, relative to a total weight of the composition being discussed.

As used herein, the term "Group VIII metals" (or "Group VIIIB metals") refers to the elements iron, ruthenium, osmium, cobalt, rhodium, iridium, nickel, palladium, and platinum. Current IUPAC naming convention may refer to these elements as Group 8, Group 9, and Group 10 elements. The name "Group VIII" remains in common use due to historical widespread use. The same set of elements was frequently referred to as group "VIIIB" in the Chemical Abstracts Service (CAS) "U.S. system" or "Group VIII" in the old IUPAC (pre-1990) "European system".

As used herein, the term "dehydrogenation" refers to a chemical reaction that involves removal of hydrogen from an organic molecule. In addition, "oxidative dehydrogenation" refers to a chemical reaction that involves the removal of hydrogen from an organic molecule in the presence of an oxidant such as molecular oxygen. Distinct from "oxidative dehydrogenation" is "oxidative cracking", which is distinguished by the breaking of carbon-carbon bonds and the loss of one or more carbon atoms from the material which is oxidatively cracked. In aspects of the present disclosure, oxidative cracking of an alkane affords an olefin having one fewer carbon atom. For example, when a propane-containing hydrocarbon stream is contacted with an appropriate catalyst in the presence of an oxidant such as oxygen gas under appropriate reaction conditions, the propane is said to be "oxidatively dehydrogenated" to afford propene, whereas the propane is said to be "oxidatively cracked" to form ethylene. These processes may take place simultaneously, the ratio of the oxidative dehydrogenation to the oxidative cracking being dependent upon the reaction conditions and/or catalyst. As a result, the reaction of a propane-containing hydrocarbon stream may produce a product stream that includes, among other components, ethylene and propylene. Examples of such "other components" include, but are not limited unreacted propane, carbon dioxide, and carbon monoxide. As used herein, a method of oxidative cracking a hydrocarbon refers to a method which produces more oxidative cracking than oxidative dehydrogenation, in terms of consumption of the hydrocarbon.

According to a first aspect, the present disclosure relates to a nanomaterial catalyst, comprising a partially crystalline porous magnesium silicate support which is substantially free of titanium and aluminum, and has gold nanoparticles dispersed thereon. The nanomaterial catalyst is substantially free of Group VIII metals. Accordingly, both the partially crystalline porous magnesium silicate support and the gold nanoparticles are both substantially free of Group VIII metals. In some embodiments, the nanomaterial catalyst is devoid of Group VIII metals. In such embodiments, accordingly both the partially crystalline porous magnesium silicate support and the gold nanoparticles are both devoid of Group VIII metals.

In general, the partially crystalline porous magnesium silicate support may be constructed of any porous magnesium silicate known to one of ordinary skill in the art. Magnesium silicates are frequently described using a chemical formula of MgO:XSiO$_2$, where X denotes the average mole ratio of SiO$_2$ to MgO (or alternatively the average mole ratio of Si to Mg), or YMgO:XSiO$_2$, where X and Y are integers, the ratio of which is or approximates the mole ratio of SiO$_2$ to MgO in the material. In some embodiments, the porous magnesium silicate is anhydrous. In alternative embodiments, the porous magnesium silicate is a hydrated magnesium silicate. Hydrated magnesium silicates may also be referred to as "magnesium silicate hydrate" or MSH. In some embodiments, the partially crystalline porous magnesium silicate support has a Mg to Si molar ratio of 1:1 to 5:1, preferably 1.25:1 to 4.75:1, preferably 1.5:1 to 4.5:1, preferably 1.75:1 to 4.25:1, preferably 2:1 to 4:1, preferably 2.1:1 to 3.9:1, preferably 2.2:1 to 3.8:1, preferably 2.25:1 to 3.75:1, preferably 2.3:1 to 3.7:1, preferably 2.4:1 to 3.6:1, preferably 2.5:1 to 3.5:1, preferably 2.6:1 to 3.4:1, preferably 2.7:1 to 3.3:1, preferably 2.75:1 to 3.25:1, preferably 2.8:1 to 3.2:1, preferably 2.9:1 to 3.1:1. In some embodiments, the magnesium silicate support is devoid of aluminum and titanium. In some embodiments, the magnesium silicate support is devoid of aluminum and substantially free of titanium. In alternative embodiments, the magnesium silicate support is devoid of titanium and substantially free of aluminum. In general, the elemental composition of the partially crystalline porous magnesium silicate support, including the Mg to Si molar ratio, may be determined by any suitable technique known to one of ordinary skill in the art. Examples of suitable such techniques include mass spectrometry techniques such as inductively-coupled plasma mass spectrometry (ICP-MS), atomic emission spectroscopy techniques such as inductively-coupled plasma atomic emission spectroscopy (ICP-AES) (also referred to as ICP optical emission spectroscopy, ICP-OES), atomic absorption spectroscopy techniques such as inductively-coupled plasma atomic absorption spectroscopy (ICP-AAS), and X-ray spectroscopy techniques such as X-ray photoelectron spectroscopy.

Magnesium silicates are materials which comprise SiO$_4$ tetrahedra joined together by magnesium ions. The SiO$_4$ tetrahedra in magnesium silicates may in general adopt any structural motif present in other silicate materials, such as isolated tetradhedra as in neosilicates (single tetrahedra, also called orthosilicates) and sorosilicates (double tetrahedra), chains of tetrahedra such as inosilicates (both single chain as in pyroxene group silicates and double chain as in amphibole group silicates), rings of tetrahedra as in cyclosilicates, sheets of tetrahedra as in phyllosilicates, and three-dimensional frameworks as in tectosilicates. The arrangement of isolated tetrahedra, chains of tetrahedra, sheets of tetrahedra, or three-dimensional frameworks may give rise to channels, pores, cages, or other spaces within the magnesium silicate which is capable of hosting material which is not the magnesium silicate. Examples of materials, particularly those relevant to the current disclosure, include water, hydrocarbons, and gold nanoparticles. While the larger structures formed of tetrahedra (i.e. chains, rings, sheets, and three-dimensional frameworks) may themselves be ordered, the arrangement of these larger structures may be disordered. Such disorder may give rise to a material which is amorphous by techniques for determining crystallinity or crystal structure such as powder X-ray diffraction (PXRD). Alternatively, the larger structures may be ordered, giving rise to a crystalline material.

In some embodiments, the partially crystalline porous magnesium silicate support is a zeolitic material. As used herein, the term "zeolitic material" refers to a material having the crystalline structure or three-dimensional framework of, but not necessarily the elemental composition of, a zeolite. Zeolites are porous silicate or aluminosilicate minerals that occur in nature. Elementary building units of zeolites are SiO$_4$ (and if appropriate, AlO$_4$) tetrahedra. Adjacent tetrahedra are linked at their corners via a common oxygen atom, which results in an inorganic macromolecule with a three-dimensional framework (frequently referred to as the zeolite framework). The three-dimensional framework of a zeolite also comprises channels, channel intersections, and/or cages having dimensions in the range of 0.1-10 nm, preferably 0.2-5 nm, more preferably 0.2-2 nm. Water molecules may be present inside these channels, channel intersections, and/or cages. Zeolites which are devoid of aluminum may be referred to as "all-silica zeolites" or "aluminum-free zeolites". Some zeolites which are substantially free of, but not devoid of, aluminum are referred to as "high-silica zeolites". Some zeolites which comprise magnesium incorporated into the crystalline structure of three-dimensional framework of the zeolite are referred to as "MgO-modified zeolites". This terminology is frequently used to distinguish such materials from zeolites which contain magnesium as Mg$^{2+}$ ions or polyatomic ions disposed in the pores of the zeolite. Sometimes, the term "zeolite" is used to refer exclusively to aluminosilicate materials, excluding aluminum-free zeolites or all-silica zeolites as well as MgO-modified zeolites. According to such usage, the aluminum-free zeolites or all-silica zeolites as well as MgO-modified zeolites may be referred to as zeolitic materials. In some embodiments, the partially crystalline porous magnesium silicate support is an MgO-modified zeolite.

In some embodiments, the partially crystalline porous magnesium silicate support is a zeolitic material having a three-dimensional framework that is at least one zeolite framework selected from the group consisting of a 4-membered ring zeolite framework, a 6-membered ring zeolite framework, a 10-membered ring zeolite framework, and a 12-membered ring zeolite framework. The partially crystalline porous magnesium silicate support may have a natrolite framework (e.g. gonnardite, natrolite, mesolite, paranatrolite, scolecite, and tetranatrolite), edingtonite framework (e.g. edingtonite and kalborsite), thomsonite framework, analcime framework (e.g. analcime, leucite, pollucite, and wairakite), phillipsite framework (e.g. harmotome), gismondine framework (e.g. amicite, gismondine, garronite, and gobbinsite), faujasite framework (e.g. faujasite-series, Linde type X, and Linde type Y), mordenite framework (e.g. maricopaite and mordenite), heulandite framework (e.g. clinoptilolite and heulandite-series), stilbite framework (e.g. barrerite, stellerite, and stilbite-series), brewsterite framework, or cowlesite framework. In some embodiments, the partially crystalline porous magnesium silicate support is substantially free of material having a chabazite framework (e.g. chabazite-series, herschelite, willhendersonite, and SSZ-13). In some embodiments, the partially crystalline porous magnesium silicate support is devoid of material having a chabazite framework. In some embodiments, the partially crystalline porous magnesium silicate support is a zeolitic material having a zeolite framework selected from the group consisting of ZSM-5, ZSM-8, ZSM-11, ZSM-12, ZSM-18, ZSM-23, ZSM-35 and ZSM-39. It should be noted here that the partially crystalline porous magnesium silicate support being substantially free of titanium and aluminum should be understood to refer to aluminum and titanium which are incorporated into the structure of the magnesium silicate support or are present as ions disposed on the magnesium silicate support, for example in the pores. It should be understood that aluminum and/or titanium which is present in the gold nanoparticles, for example as an alloy or as a core as part of a core-shell nanoparticle structure, should not be considered to be part of the partially crystalline porous magnesium silicate support. Such aluminum and/or titanium present may be considered part of the gold nanoparticles.

In some embodiments, the partially crystalline porous magnesium silicate support is amorphous by PXRD. In such embodiments, the partially crystalline porous magnesium silicate support may have local, short-range ordering, but lacks the long-range order characteristic of a crystal. In such embodiments, the partially crystalline porous magnesium silicate support is crystalline or partially crystalline by an electron microscopy technique, such as TEM. In some embodiments, the partially crystalline porous magnesium silicate support is a single crystalline phase by PXRD. This single crystalline phase may be indexed to a material which is magnesium silicate or a magnesium silicate material. This single crystalline phase is preferably not a crystalline form of silica or magnesium oxide. The single crystalline phase being indexed to a crystalline form of silica or magnesium oxide would indicate the presence of phase separation in the partially crystalline porous magnesium silicate support. In preferred embodiments, the partially crystalline porous magnesium silicate support is devoid of a crystalline MgO phase by PXRD. In some embodiments, the partially crystalline porous magnesium silicate is poorly crystalline by PXRD. In preferred embodiments, the partially crystalline porous magnesium silicate support has two or more peaks, preferably three or more peaks, preferably four or more peaks in the PXRD at a 2θ angle of 17.5 to 27.5°+0.2°. In such embodiments, the peaks are preferably chosen from the group consisting of approximately 17.5° to approximately 20.4°, approximately 20.5° to approximately 22.5°, approximately 22.6 to approximately 24.3°, and approximately 24.5° to approximately 27.5°. In some embodiments, the partially crystalline porous magnesium silicate support has a single peak in the PXRD at a 2θ angle of 32.5 to 37.5° 0.2°. In some embodiments, the partially crystalline porous magnesium silicate support has a single peak in the PXRD at a 2θ angle of 57.5 to 62.5°+0.2°. In preferred embodiments, the partially crystalline porous magnesium silicate support has two or more peaks in the PXRD at a 2θ angle of 17.5 to 27.5°+0.2°, a single peak in the PXRD at a 2θ angle of 32.5 to 37.5° 0.2°, and a single peak in the PXRD at a 2θ angle of 57.5 to 62.5°+0.2°. As used herein, "poorly crystalline" or "partially crystalline" refers to a material which comprises both crystalline and amorphous portions or regions which have substantially the same elemental composition. One metric for defining poorly crystalline materials is the degree of crystallinity. The degree of crystallinity refers to the percentage or fraction of crystalline portions or regions out of the entirety of the material. The degree of crystallinity may be calculated from PXRD data by dividing the total intensity or area contributed to the overall diffraction pattern by the crystalline material by the sum of said intensity or area and the total intensity or area contributed to the overall diffraction pattern by the amorphous material. In some embodiments, the partially crystalline porous magnesium silicate support has a degree of crystallinity of 0.07 to 0.9, preferably 0.1 to 0.8, preferably 0.15 to 0.7, preferably 0.2 to 0.75, preferably 0.25 to 0.6. An example of a partially crystalline porous magnesium silicate support which is not suitable by PXRD and/or crystallinity may be found in Shylesh, et al. [S. Shylesh, A. A. Gokhale, C. D. Scown, D. Kim, C. R. Ho, A. T. Bell, ChemSusChem, 9 (2016) 1462-1472].

In some embodiments, the partially crystalline porous magnesium silicate support has an average crystallite size of 5 to 50 nm, preferably 7.5 to 45 nm, preferably 10 to 40 nm, preferably 12.5 to 35 nm, preferably 15 to 30 nm by PXRD. In some embodiments, a plurality of crystallites may be agglomerated or aggregated into larger particles, for instance, particles having an average particle diameter of 0.25-5.0 μm, preferably 0.5-2.5 μm, preferably 1-2 μm. In other embodiments, the crystals of the porous magnesium silicate may be agglomerated or aggregated into particles having an average particle diameter of less than 0.25 μm or greater than 5.0 μm. In some embodiments, the partially crystalline porous magnesium silicate support may be in the form of particles which comprise both crystalline and amorphous portions or regions, the crystalline regions having a crystallite size as described above. In such embodiments, the particles may have a particle size as described above.

In some embodiments, the gold nanoparticles are present in an amount of 0.1 to 5 wt. %, preferably 0.15 to 4.5 wt. %, preferably 0.2 to 4 wt. %, preferably 0.25 to 3.75 wt. %, preferably 0.3 to 3.5 wt. %, preferably 0.35 to 3.25 wt. %, preferably 0.4 to 3 wt. %, preferably 0.425 to 2.75 wt. %, preferably 0.45 to 2.5 wt. %, preferably 0.475 to 2.25 wt. %, preferably 0.5 to 2 wt. %, based on a total weight of nanomaterial catalyst. In general, the gold nanoparticles may be any suitable gold nanoparticles known to one of ordinary skill in the art. To be considered "gold nanoparticles" it is envisioned that the nanoparticles be comprised of mostly gold (i.e. greater than 50%, more preferably greater than 60%, more preferably greater than 70%, more preferably greater than 75%, more preferably greater than 80%, more preferably greater than 85%, more preferably greater than 90%, more preferably greater than 95%, most preferably greater than 99% gold by weight). In addition to gold, various other non-gold materials including, but not limited to, alloys, metals, metalloids, and non-metals may be present in the gold nanoparticles. The total weight of these non-gold materials relative to the total weight percentage of the gold in the nanoparticles is typically less than 30%, preferably less than 20%, preferably less than 15%, preferably less than 10%, more preferably less than 5%, more preferably less than 4%, more preferably less than 3%, more preferably less than 2%, more preferably less than 1%.

In addition to gold, it is envisaged that the present disclosure may be adapted to incorporate gold alloys as the gold nanoparticles. Exemplary alloys include, but are not limited to: gold alloys with copper (rose gold, tumbaga), gold alloys with copper and silver (colored gold, crown gold, electrum), gold alloys including the addition of manganese, aluminum, indium, titanium, zinc, cadmium, and other appropriate elements or mixtures thereof. Alloys which are not suitable are alloys which contain Group VIII metals, such as gold alloys with rhodium (rhodite), gold alloys with nickel and palladium (white gold), and other gold alloys including the addition of ruthenium, osmium, cobalt, rhodium, iridium, nickel, palladium, platinum, and mixtures thereof. In one embodiment, it is envisaged that the present disclosure may be adapted in such a manner that the gold nanoparticles substantially comprise a gold alloy. It should be noted that aluminum and titanium may be incorporated into the gold nanoparticle, for example as a core material in a core-shell nanoparticle or as a constituent in a gold alloy. Such content of aluminum and/or titanium should not be considered part of the partially crystalline porous magnesium silicate support.

In some embodiments, it is envisioned that the gold nanoparticles be of a composition and be dispersed on the partially crystalline porous magnesium silicate support such that the hydrocarbon may interact directly with a surface of the gold nanoparticle, said surface being comprised of mostly gold as described above. For example, gold nanoparticles having a non-porous silica coating which encompasses an entirety of the gold nanoparticle would not allow for the hydrocarbon to interact with the surface of the gold nanoparticle (the hydrocarbon would instead interact with the surface of the silica coating). An additional example which is not envisioned as suitable in any embodiments is a core-shell nanoparticle structure in which gold forms the core of the nanoparticle and the shell of the nanoparticle is a non-porous material, such as a metal or metal oxide (e.g. silver or iron oxide). An example which is envisioned as suitable is a core-shell nanoparticle in which gold forms the shell of the nanoparticle, such as gold nanoshells.

In general, the gold nanoparticles can be any shape known to one of ordinary skill in the art. Examples of suitable shapes the gold nanoparticles may take include spheres, spheroids, lentoids, ovoids, solid polyhedra such as tetrahedra, cubes, octahedra, icosahedra, dodecahedra, hollow polyhedral (also known as nanocages), stellated polyhedral (both regular and irregular, also known as nanostars), triangular prisms (also known as nanotriangles), hollow spherical shells (also known as nanoshells), tubes (also known as nanotubes), nanosheets, nanoplatelets, nanodisks, rods (also known as nanorods), and mixtures thereof. In the case of nanorods, the rod shape may be defined by a ratio of a rod length to a rod width, the ratio being known as the aspect ratio. For gold nanoparticles of the current invention, nanorods should have an aspect ratio less than 1000, preferably less than 750, preferably less than 500, preferably less than 250, preferably less than 100, preferably less than 75, preferably less than 50, preferably less than 25. Nanorods having an aspect ratio greater than 1000 are typically referred to as nanowires and are not a shape that the gold nanoparticles are envisioned as having in any embodiments.

In some embodiments, the gold nanoparticles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of gold nanoparticles having a different shape. As used herein, the term "non-uniform shape" refers to an average consistent shape that differs by more than 10% of the distribution of gold nanoparticles having a different shape. In one embodiment, the shape is uniform and at least 90% of the gold nanoparticles are spherical or substantially circular, and less than 10% are polygonal. In another embodiment, the shape is non-uniform and less than 90% of the gold nanoparticles are spherical or substantially circular, and greater than 10% are polygonal.

In some embodiments, the gold nanoparticles have an average particle size of 5 to 100 nm, preferably 7.5 to 75 nm, preferably 10 to 60 nm, preferably 12.5 to 50 nm, preferably 15 to 40 nm, preferably 15.5 to 35 nm, preferably about 16 to 32 nm. In embodiments where the gold nanoparticles are spherical, the particle size may refer to a particle diameter. In embodiments where the gold nanoparticles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments, where the gold nanoparticles have an anisotropic shape such as nanorods, the particle size may refer to a length of the nanorod, a width of the nanorod, an average of the length and width of the nanorod. In some embodiments in which the gold nanoparticles have non-spherical shapes, the particle size refers to the diameter of a sphere having an equivalent volume as the particle. In some embodiments in which the gold nanoparticles have non-spherical shapes, the particle size refers to the diameter of a sphere having an equivalent diffusion coefficient as the particle.

In some embodiments, the gold nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the gold nanoparticles of the present disclosure are monodisperse having a particle size distribution ranging from 80% of the average particle size to 120% of the average particle size, preferably 90-110%, preferably 95-105% of the average particle size. In some embodiments, the gold nanoparticles are not monodisperse.

In general, the particle size may be determined by any suitable method known to one of ordinary skill in the art. In some embodiments, the particle size is determined by powder X-ray diffraction (PXRD). Using PXRD, the particle size may be determined using the Scherrer equation, which relates the full-width at half-maximum (FWHM) of diffraction peaks to the size of regions comprised of a single crystalline domain (known as crystallites) in the sample. In some embodiments, the crystallite size is the same as the particle size. For accurate particle size measurement by PXRD, the particles should be crystalline, comprise only a single crystal, and lack non-crystalline portions. Typically, the crystallite size underestimates particle size compared to other measures due to factors such as amorphous regions of particles, the inclusion of non-crystalline material on the surface of particles such as bulky surface ligands, and particles which may be composed of multiple crystalline domains. In some embodiments, the particle size is determined by dynamic light scattering (DLS). DLS is a technique which uses the time-dependent fluctuations in light scattered by particles in suspension or solution in a solvent, typically water to measure a size distribution of the particles. Due to the details of the DLS setup, the technique measures a hydrodynamic diameter of the particles, which is the diameter of a sphere with an equivalent diffusion coefficient as the particles. The hydrodynamic diameter may include factors not accounted for by other methods such as non-crystalline material on the surface of particles such as bulky surface ligands, amorphous regions of particles, and surface ligand-solvent interactions. Further, the hydrodynamic diameter may not accurately account for non-spherical particle shapes. DLS does have an advantage of being able to account for or more accurately model solution or suspension behavior of the particles compared to other techniques. In some embodiments, the particle size is determined by electron microscopy techniques such as scanning electron microscopy (SEM) or transmission electron microscopy (TEM).

In some embodiments, the nanomaterial catalyst has a surface area of 300 to 500 $m^2/g$, preferably 310 to 490 $m^2/g$, preferably 315 to 475 $m^2/g$, preferably 320 to 450 $m^2/g$, preferably 325 to 440 $m^2/g$, preferably 330 to 430 $m^2/g$, preferably 335 to 425 $m^2/g$. In general, the surface area may be determined using any suitable technique known by one of ordinary skill in the art. Examples of such techniques include, but are not limited to, calculations from particle size distribution, gas adsorption techniques, and gas permeability techniques. In some embodiments, the surface area is determined by a gas adsorption technique. The gas used in the gas adsorption technique may be any suitable gas known to one of ordinary skill in the art, for example nitrogen, helium, carbon dioxide, carbon monoxide, water, and krypton. In some embodiments, the surface area is a BET surface area. In preferred embodiments, the surface area is an $N_2$-BET surface area. In some embodiments, the nanomaterial catalyst has a has an average pore size of 1 to 25 nm, preferably 2 to 22.5 nm, preferably 3 to 20 nm, preferably 4 to 17.5 nm, preferably 5 to 15 nm. In preferred embodiments, the pore size is determined by a gas adsorption technique as described above. In some embodiments, the nanomaterial catalyst has a pore volume of 0.225 to 0.375 cm$^3$/g, preferably 0.230 to 0.360 cm$^3$/g, preferably 0.235 to 0.350 cm$^3$/g, preferably 0.240 to 0.345 cm$^3$/g, preferably 0.250 to 0.335 cm$^3$/g, preferably 0.260 to 0.325 cm$^3$/g, preferably 0.262 to 0.321 cm$^3$/g. In preferred embodiments, the pore volume is determined by a gas adsorption technique as described above.

In some embodiments, the nanomaterial catalyst has an acidity of 7.5 to 30 mmol/g, preferably 8 to 29 mmol/g, preferably 8.5 to 28 mmol/g, preferably 9 to 27 mmol/g, preferably 9.5 to 26 mmol/g, preferably 10 to 25 mmol/g, preferably 10.5 to 24 mmol/g. In some embodiments, the acidity is a total acidity. The total acidity may be the sum of a Lewis acidity and a Brønsted acidity. In some embodiments, the nanomaterial catalyst has a ratio of Lewis acidity to Brønsted acidity of 1:1 to 100:1, preferably 10:1 to 75:1, preferably 25:1 to 50:1, preferably 29:1 to 40:1. In general, the acidity may be measured by any suitable technique known to one of ordinary skill in the art. Examples of such techniques include Hammett's indicator titration, microcalorimetry of adsorbed probe molecules (ammonia, pyridine or other amines), ammonia or amine thermodesorption, IR spectroscopy of hydroxyl groups and of several probe molecules adsorbed (such as ammonia, pyridine, piperidine, amines, CO, and $H_2$), and Magic Angle Spinning Nuclear Magnetic Resonance (MAS-NMR) of $^{29}$Si, $^1$H, or other suitable nucleus of elements within the structure of the nanomaterial catalyst or of $^1$H, $^{13}$C, $^{31}$P, or other suitable nucleus of adsorbed probe molecules. In preferred embodiments, the acidity is measured by IR spectroscopy of adsorbed amines, preferably pyridine.

In some embodiments, the nanomaterial catalyst consists of the partially crystalline porous magnesium silicate support having a Mg to Si molar ratio of 1:1 to 5:1, and the gold nanoparticles having an average particle size of 5 to 100 nm dispersed on the partially crystalline porous magnesium silicate support, wherein the nanomaterial catalyst has a surface area of 300 to 500 m$^2$/g, a pore volume of 0.225 to 0.375 cm$^3$/g, and an acidity of 7.5 to 30 mmol/g, as described above.

The present disclosure also relates to a method for making the nanomaterial catalyst described above, the method comprising reacting a magnesium salt, colloidal silica, and a first solvent under solvothermal conditions at 120 to 200° C., preferably 130 to 190° C., preferably 140 to 180° C., preferably 150 to 170° C., preferably 160° C. for 2 to 24 hours, preferably 4 to 20 hours, preferably 6 to 16 hours, preferably 8 to 12 hours, preferably 9 to 11 hours, preferably 10 hours to produce a first precipitate, calcining the first precipitate at 250 to 750° C., preferably 300 to 700° C., preferably 350 to 650° C., preferably 400 to 600° C., preferably 425 to 575° C., preferably 450 to 550° C., preferably 475 to 525° C., preferably 500° C. to produce the partially crystalline porous magnesium silicate support, adding a gold precursor to a dispersion comprising the partially crystalline porous magnesium silicate support in a second solvent to produce a reduction mixture, heating the reduction mixture to 70 to 100° C., preferably 75 to 95° C., preferably 80 to 90° C. for 60 to 360 minutes, preferably 75 to 300 minutes, preferably 90 to 240 minutes, preferably 105 to 180 minutes, preferably 120 minutes to produce a second precipitate, and calcining the second precipitate at 250 to 750° C., preferably 300 to 700° C., preferably 350 to 650° C., preferably 400 to 600° C., preferably 425 to 575° C., preferably 450 to 550° C., preferably 475 to 525° C., preferably 500° C. to produce the nanomaterial catalyst.

As used herein, the term "solvothermal conditions" refers to conditions of a chemical reaction involving reacting reagents in a solvent other than pure water, preferably at a pressure above 1 bar and at a temperature above the boiling point of the solvent at atmospheric pressure. Solvothermal conditions differ from hydrothermal conditions in that the latter is restricted to using only water as the solvent. Typically, if water is the only solvent used, the term hydrothermal is preferred and solvothermal refers solely to methods that use solvents other than or in addition to water. In some embodiments, the first solvent is water. In some embodiments, the first solvent is a mixture of water and an organic solvent miscible with water. In some embodiment, the second solvent is a mixture of water and an organic solvent miscible with water. Examples of organic solvents which are miscible with water include, but are not limited to acetaldehyde, acetic acid, acetone, acetonitrile, 1,2-butanediol, 1,3-butanediol, 1,4-nutanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, N-methyl-2-pyrrolidone, 1-propanol, 1,3-propanediol, 1,5-pentanediol, 2-propanol, propanoic acid, propylene glycol, pyridine, tetrahydrofuran, and triethylene glycol. In preferred embodiments, the first and second solvent are mixtures of water and ethanol having a water-to-ethanol volumetric ratio of 3:1 to 1:3, preferably 2.5:1 to 1:2.5, preferably 2:1 to 1:2.25, preferably 1.5:1 to 1:2, preferably 1.25:1 to 1:1.75, preferably 1:1 to 1:1.6, preferably 1:1.5.

In general, the magnesium salt may be any water-soluble magnesium salt or one that is soluble in a solvent miscible with water listed above. Examples of such magnesium salts include, but are not limited to magnesium nitrate, magnesium acetate, magnesium chloride, magnesium bromide, magnesium iodide, magnesium chlorate, magnesium perchlorate, magnesium sulfate, magnesium sulfite, and magnesium nitrite. In preferred embodiments, the magnesium salt is magnesium nitrate. In general, the gold precursor may be any suitable gold precursor for the preparation of gold nanoparticles known to one of ordinary skill in the art. Examples of such gold precursors include, but are not limited to gold (III) chloride, gold (III) bromide, gold (III) iodide, gold (I) chloride, gold (I) bromide, gold (I) iodide, gold (III) acetate, and potassium gold cyanide. These gold precursors may also be referred to as gold salts. In preferred embodiments, the gold precursor is gold (III) chloride, gold (III) acetate, or a mixture thereof.

In some embodiments, the adding of the gold precursor comprises injection of a gold solution comprising the gold precursor in a third solvent into the dispersion at a temperature of 70 to 100° C., preferably 75 to 95° C., preferably 80 to 90° C.

The present disclosure also relates to a method for making the nanomaterial catalyst, the method comprising mixing a magnesium salt, a water-soluble silicate source, a gold salt, and a solvent to form a precursor mixture, adjusting the pH of the precursor mixture to a pH>7 to form an adjusted reaction mixture, and reacting the adjusted reaction mixture under solvothermal conditions at 160 to 200° C., preferably 165 to 195° C., preferably 170 to 190° C., preferably 175 to 185° C., preferably 180° C. for 12 to 90 hours, preferably to produce the nanomaterial catalyst. In general, the magnesium salt may be any magnesium salt as described above. In preferred embodiments, the magnesium salt is magnesium nitrate. In general, the gold salt may be any gold salt as described above. In preferred embodiments, the gold salts gold (III) chloride, gold (III) acetate, or a mixture thereof.

In general, the water-soluble silicate source may be any suitable water-soluble silicate source known to one of ordinary skill in the art. Examples of such water-soluble silicate sources include, but are not limited to colloidal silica, alkali metal metasilicates, alkali metal orthosilicates, and alkali metal pyrosilicates. In some embodiments, the water-soluble silicate source is an alkali metal metasilicate. In preferred embodiments, the water-soluble silicate source is sodium metasilicate. In alternative preferred embodiments, the water-soluble silicate source is colloidal silica. In other alternative preferred embodiments, the water soluble silicate source is a mixture of sodium metasilicate and colloidal silica.

In some embodiments, the solvent is a mixture of water and an organic solvent miscible with water as described above. In some embodiments, the organic solvent is ethanol. In some embodiments, the organic solvent is 1-propanol. In some embodiments, the organic solvent is a mixture of ethanol and 1-propanol. In preferred embodiments, the solvent is a mixture of water and an alcohol selected from the group consisting of ethanol and 1-propanol having a water-to-alcohol volumetric ratio of 1:3 to 1:1, preferably 1:2 to 1:1.25, preferably 1:1.5.

The present disclosure also relates to a method of oxidative cracking of hydrocarbon having 3 to 6 carbon atoms, comprising contacting at a temperature of 650° C. or lower, preferably 625° C. or lower, preferably 600° C. or lower, preferably 575° C. or lower, preferably 550° C. or lower, preferably 525° C. or lower, preferably 500° C. or lower the nanomaterial catalyst with a gas mixture comprising 5 to 20 vol. %, preferably 7.5 to 17.5 vol. %, preferably 10 to 15 vol. %, preferably 11 to 14 vol. %, preferably 12 to 13 vol. %, preferably 12.5 vol. % of the hydrocarbon having 2 to 6 carbon atoms, 5 to 20 vol. %, preferably 7.5 to 17.5 vol. %, preferably 10 to 15 vol. %, preferably 11 to 14 vol. %, preferably 12 to 13 vol. %, preferably 12.5 vol. % oxygen, and 60 to 90 vol. %, preferably 65 to 85 vol. %, preferably 70 to 80 vol. %, preferably 72.5 to 77.5 vol. %, preferably 75 vol. % a carrier gas, wherein the contacting produces a light olefin. In preferred embodiments, the hydrocarbon having 3 to 6 carbon atoms is propane. In some embodiments, the hydrocarbon is n-butane. In some embodiments, the hydrocarbon is 2-methylpropane (also known as isobutane). In some embodiments, the hydrocarbon is n-pentane. In some embodiments, the hydrocarbon is 2-methylbutane (also known as methylbutane or isopentane). In some embodiments, the hydrocarbon is 2,2-dimethylpropane (also known as dimethylpropane or neopentane). In some embodiments, the hydrocarbon is n-hexane. In some embodiments, the hydrocarbon is 2-methylpentane (also known as isohexane). In some embodiments, the hydrocarbon is 3-methylpentane. In some embodiments, the hydrocarbon is 2,3-dimethylbutane. In some embodiments, the hydrocarbon is 2,2-dimethylbutane (also known as neohexane). In some embodiments, a mixture of hydrocarbons is used. In such embodiments, the mixture may comprise one or more hydrocarbons having 3 to 6 carbon atoms as described above. Preferably, such mixtures comprise a majority (i.e. greater than 50% by volume or by mole) hydrocarbons having 3 to 6 carbon atoms. In some embodiments, the mixture consists of two or more hydrocarbons having 3 to 6 carbon atoms. Examples of suitable mixtures of hydrocarbons include, but are not limited to ethane-propane mixtures, propane-butanes mixtures, propane-propene mixtures, butane-butene mixtures, and propane-propene-butane-butene mixtures. Additionally, the mixture may be an industrially-relevant process stream. Such a stream may be the output of an industrial process which handles hydrocarbons such as natural gas fractionation, NGL recovery, natural gas condensate and water removal, natural gas acid gas removal, natural gas nitrogen rejection, raw natural gas production, or hydrocarbon cracking. Examples of such streams include, but are not limited to, de-ethanized liquefied petroleum gas, and de-methanized liquefied petroleum gas. In some embodiments, the hydrocarbon is provided to the nanomaterial catalyst at a gas hourly space velocity of 5,000 to 100,000 $h^{-1}$, preferably 10,000 to 75,000 $h^{-1}$, preferably 12,000 to 60,000 $h^{-1}$, preferably 24,000 to 48,000 $h^{-1}$.

Methods of oxidative cracking of hydrocarbons may be characterized by certain reaction metrics which relate to an efficiency or percentage of the hydrocarbon which is consumed or converted by contact with the catalyst. Such a conversion or consumption percentage may be measured by measuring the disappearance of the hydrocarbon. Such a conversion percentage by definition includes both the oxidative cracking reaction that produces a light olefin and other reactions which do not produce light olefins. In some embodiments, the method has a percentage conversion of the hydrocarbon having 2 to 6 carbon atoms of greater than 60%, preferably greater than 65%, preferably greater than 70%, preferably greater than 75%, preferably greater than 80%, preferably greater than 85%, preferably greater than 90% based on a total amount of hydrocarbon having 2 to 6 carbons being contacted with the nanomaterial catalyst.

As used herein, the term "olefin selectivity" refers to the percentage of the amount (by mole) of hydrocarbon that is converted to a light olefin (i.e. ethylene and/or propylene). In addition, the selectivity of oxygenation and cracking reactions refers to the amount (by mole) of hydrocarbon that is converted via oxygenation and cracking reactions, and the selectivity of partial oxidation reactions refers to the amount (by mole) of hydrocarbon that is converted via partial oxidation reactions. Alternatively, the "selectivity" is defined as a molar ratio of the combined molar amount of light olefins (i.e. ethylene and propylene) to the other compounds present in a product stream. In some embodiments, the olefin selectivity is substantially independent of the hydrocarbon conversion. In some embodiments, the method has an olefin selectivity of greater than 65%, preferably greater than 67.5%, preferably greater than 70%, preferably greater than 72.5%, preferably greater than 75%, preferably greater than 77.5%, preferably greater than 80%, preferably greater than 81%, preferably greater than 82%, preferably greater than 83%, preferably greater than 84%, preferably greater than 85%, preferably greater than 86%, preferably greater than 87%, based on a total amount of hydrocarbon having 2 to 6 carbons which is converted by contacting the nanomaterial catalyst.

In some embodiment, the nanomaterial catalyst is housed in a catalyst bed of a reactor. The reactor may preferably be a fixed-bed reactor, although other reactors such as a batch reactor or a fluidized bed reactor may also be employed. In such embodiments, the hydrocarbon, oxygen, and carrier gas may be delivered to the reactor either together as a mixed gas through a common feed line, or separately but simultaneously via different feed lines.

In some embodiments, the nanomaterial catalyst is in the form of catalyst particles. In general, the catalyst particles may be any form known to one of ordinary skill in the art. Examples of such forms the catalyst particles make take include a powder, granules, pellets, extrudates, or a shaped catalyst. In some embodiments, the catalyst particles are in the form of disc-shape pellets. Alternatively, the catalyst particles may be in the form of pellets having a cylindrical (solid or hollow cylindrical), a spherical, a rectilinear, a star-shape, a ring-shape, a conical, a pyramidal, a rectangular, or a cubical geometry. In some embodiments, the catalyst particles have an average particle size of 0.1 to 2 mm, preferably 0.2 to 1.5 mm, more preferably about 1 mm. Shaping of the catalyst particles may be carried out by compaction (for example tableting or extrusion) of a solid catalyst mixture with or without a prior kneading step, if necessary with addition of conventional auxiliaries (e.g., graphite or stearic acid or its salts as lubricants).

In some embodiments, the catalyst particles further comprise binders and/or diluents, which are known to those of skilled in the art to reduce a concentration of the nanomaterial catalyst in the catalyst particles. In some embodiments, the catalyst particles are present in the reactor. In such embodiments, the diluents may be added to the reactor as separate diluent particles. In some embodiments, diluent particle are added to the reaction in an amount of 0 to 30 vol %, preferably 5 to 25 vol %, preferably 10 to 20 vol %, relative to the total volume of a catalyst bed that houses the catalyst and the diluents. The diluents may improve the heat removal or heat transfer of the nanomaterial catalyst to help avoid hot spots or to modify hot spots. Additionally, binders may provide mechanical strength to the nanomaterial catalyst and/or catalyst particles. Such binders may be added to the nanomaterial catalyst in the range of 0 to 30 vol %, preferably 5 to 25 vol %, preferably 10 to 20 vol %, relative to the total volume of the catalyst/binder. In general, the binder and/or diluents may be any suitable material known to one of ordinary skill in the art. Examples of materials which may be binders and/or diluents include silica sol, silica, alumina, diatomaceous earth, hydrated zirconia, silica aluminas, alumina phosphates, naturally occurring materials, cements and combinations thereof. Preferable diluents include, for example, quartz chips, sands, clay and/or cement.

The examples below are intended to further illustrate protocols for and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

EXAMPLES

Partially Crystalline Porous Magnesium Silicate Nanomaterial

The partially crystalline porous magnesium silicate nanomaterial synthesized by a simple hydrothermal method using mixed water/ethanol solvent. Stoichiometric quantities of commercially available Ludox SM colloidal silica (30 wt. % $SiO_2$, 0.56 wt. % $Na_2O$) and $Mg(NO_3)_2 \cdot 6H_2O$ dissolved in calculated amount of $H_2O$. To this solution, a calculated amount of KOH was added to adjust the pH (between 10 and 11) of the total contents and then the total solution was poured into a Teflon-lined autoclave and hydrothermally treated at 160° C. for 10 h. The obtained precipitate was filtered and washed with double distilled water until the pH of the water is neutral and the filtered materials was dried at 80° C. in static air. Finally, the dried material was thermally treated at 500° C. for 4 h.

Gold Decorated Partially Crystalline Porous Magnesium Silicate Nanomaterials

A reflux-reduction method was adopted to deposit the gold nanoparticles over the surface of magnesium silicate nanomaterial and in a typical synthesis, calculated amount of magnesium silicate nanomaterial was dispersed into a 100 mL mixed-solution with water: ethanol=2:3 to form a mixture, which was refluxed for about half an hour, then calculated amount aqueous gold chloride solution corresponding to gold weight percentage was injected into the mixture, which was turned black quickly. After two hours, the mixture was cooled to room temperature, filtered, washed, dried at 80° C. and then calcined at 500° C. for 4 h.

Characterization of Catalysts

A systematic catalyst characterization was performed to investigate the physico-chemical properties of the samples using different techniques. The elemental composition of the synthesized materials was determined by using ICP-AES (Optima 7300DV, Perkin-Elmer) instrument. The XRD patterns of the powders were collected by using PANalytical XpertPro diffractometer. The crystallite size of obtained materials were determined by applying the Debye-Scherer equation. The SEM analysis of the samples was performed using JEOL Model JSM-6390LV microscope. The DRIFT spectra of calcined materials were obtained using Bruker vertex 70 FT-IR spectrometer. The acidic character of the samples was investigated by pyridine adsorption measurements using DRIFT technique; the analysis was performed over calculated amount of catalyst, which will be treated at 100° C. under vacuum for 5 h. Then, the sample was treated with pyridine vapor and finally heated at 100° C. under vacuum for 30 min to remove physically adsorbed pyridine. The XPS spectra of the materials were collected by using Kratos Axis Nova spectrometer. The textural properties of the samples were obtained from the $N_2$-physisorption experiments, which were conducted using Quantachrome ASiQ adsorption system. The $H_2$-TPR, $O_2$-TPD and CO chemisorption experiments were performed by using Quantachrome CHEMBET-3000 system. The detailed procedures were provided in Narasimharao, et al. and Alshehri, et al. [K. Narasimharao, A. Alshehri, Fuel, 278 (2020)118375; and A. Alshehri, K. Narasimharao, J. Mater. Res. Technol. 9 (2020) 14907-14921].

Oxidative Cracking of n-Propane

The synthesized catalysts are evaluated for oxidative cracking of n-propane measurements using a fixed bed quartz reactor. The reactor was loaded with weighed catalyst pellets (200 mg), which were diluted with unreactive quartz particles. The reactant gas mixture, which contained n-propane (20 mL min$^{-1}$), 20% oxygen-80% argon (100 mL min$^{-1}$) and argon (40 mL min$^{-1}$) will be used to perform the catalytic tests. Different reaction temperatures will be used to investigate the effect of reaction temperature on the catalyst performance. The composition of product gas mixture will be continuously analyzed with the assistance of Agilent 6890 A gas chromatograph equipped with flame ionization and thermal conductivity detectors.

Results and Discussion

The powder XRD patterns of calcined MgSil and Au/MgSil materials are presented in FIG. 1. The bulk MgSil sample exhibited broad and low intense reflections corresponding to the partially crystalline magnesium silicate phase [JCPDS. 02-1009]. The observed reflections are also consistent with the XRD pattern of magnesium-silicate-hydrate by Brew and Glasser [D. R. M. Brew, F. P. Glasser, Cem. Concr. Res. 35 (2005) 85-98]. The XRD pattern of MgSil sample have not exhibited any additional sharp reflections due to MgO/Mg(OH)$_2$ or broad humps corresponding to amorphous SiO$_2$, revealing that the synthesized sample is composed of only magnesium silicate phase.

The XRD patterns of Au/MgSil samples exhibited sharp major reflections at 38.3°, 44.3°, 65.4°, 77.5° corresponding to (111), (200), (220) and (311) crystal planes of face-centered cubic (fcc) Au crystals [JCPDS No. 04-0784]. The intensity of reflection of (111) plane is much higher than the other reflections due to other crystalline planes revealing the highly crystalline nature of decorated gold particles. It is also clear that the intensities of reflections due to MgSil were decreased, while the intensities of XRD reflections due to gold nanoparticles are increased with increase of gold loading from 0.5 to 2.0 wt. %. This observation indicating the deposition of gold crystallites beyond the monolayer coverage. The sizes of the gold crystallites were determined using width broadening of the (111) Bragg reflection of gold crystalline phase by applying the Debye-Scherrer expression and obtained results are presented in Table 1. As shown in the table, the gold crystallite was increased with increase of gold loading; the 0.5Au/MgSil sample possessed the gold crystallite size of 16.5 nm, while the 2.0Au/MgSil sample contained the gold crystallite size of 24.1 nm.

The FT-IR spectroscopy is a useful tool to investigate structural properties of the amorphous or crystalline metal silicates, as it provides vital information regarding the functional groups and local atomic structure [W. R. Taylor, Proc. Indian Acad. Sci. (Earth Planet. Sci.), 99 (1990) 99-117]. It is clear that FT-IR spectrum of calcined bare MgSil and Au/MgSil samples shows a major broad absorption band at 1064 cm$^{-1}$ corresponding to anti-symmetric stretching vibration of Si—O—Mg and a minor band at 790 cm$^{-1}$ due to SiO vibrations [J. Madejová, Vib. Spectrosc. 31 (2003) 1-10]. This observation indicating that the samples contained the layer-structured magnesium silicate and framework silica atoms. The low intense bands appeared at 560 and 660 cm$^{-1}$ could be ascribed to symmetric stretching vibration of Si—O—Mg of MgSil framework [M. Singh, L. Singh, Indian J. Pure Appl. Phys. 54 (2016)116-122]. The small band at 1635 cm$^{-1}$ could be assigned to O-H stretching vibrations.

The morphology of the synthesized MgSil and Au/MgSil samples was investigated using FESEM analysis and the obtained images are shown in FIGS. 3A-3E. The FESEM image of bare MgSil sample showed the presence of partially crystalline layered magnesium silicate material along with the plain spherical agglomerates. The images of Au/MgSil samples clearly showed the presence of homogeneously dispersed gold nanoparticles, which were appeared as the bright spots on the magnesium silicate surface. The average Au particle size is in the range of 18-22 nm with high dispersion (59%, supposing spherical gold nanoparticles). The average size of the Au nanoparticles determined from XRD patterns confirmed the data analyzed from SEM images. It is also clear from the images that increase of Au loading influenced the density of Au nanoparticles. Presence of fairly dispersed gold nanoparticles could observed in case of 0.5, 1.0 and 1.5 wt. % Au loaded samples, while a highly dense packing of gold particles (relatively big size) is observed in case of 2.0Au/MgSil sample, thus supporting the XRD and UV-vis results.

TABLE 1

Crystalline and particle sizes determined from XRD and FESEM results

| Catalyst | Crystallite size (nm) | | Particle size (nm) | |
| --- | --- | --- | --- | --- |
| | MgSil | Au | MgSil | Au |
| MgSil | 28.2 | — | 34.3 | — |
| 0.5 Au/MgSil | 25.5 | 16.5 | 32.4 | 20.3 |
| 1.0 Au/MgSil | 22.1 | 19.2 | 30.7 | 23.1 |
| 1.5 Au/MgSil | 18.4 | 22.7 | 28.1 | 27.5 |
| 2.0 Au/MgSil | 15.6 | 24.1 | 25.2 | 30.6 |

Figure 4:
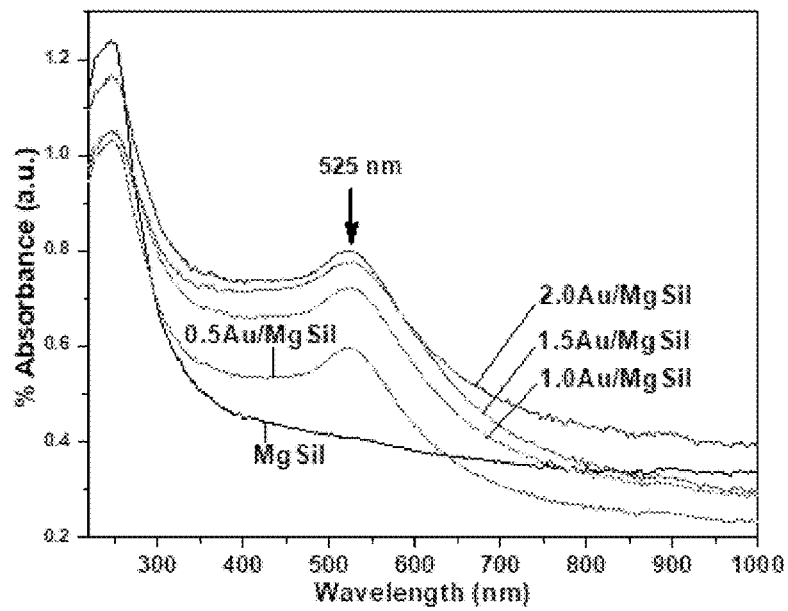
FIG. 4 shows diffuse reflectance UV-vis spectra of the Au/MgSil samples.
Figure 5A:
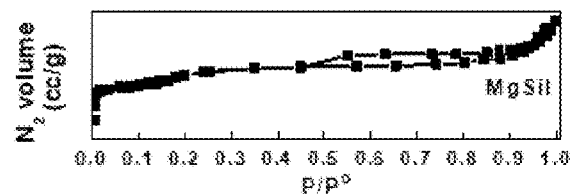
FIGS. 5A-5E show $N_2$ adsorption-desorption isotherms for Au/MgSil samples, where
Figure 5B:
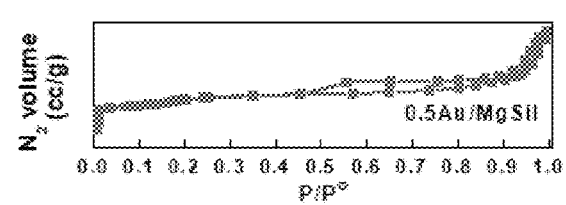
Figure 5C:
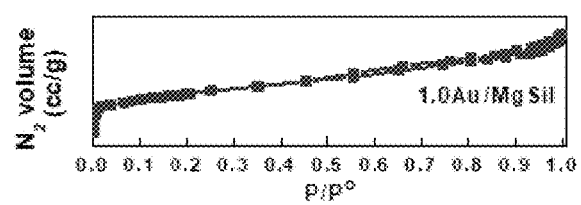
Figure 5D:
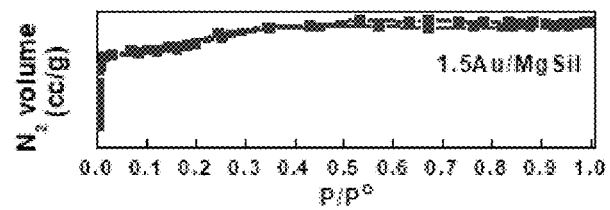
Figure 5E:
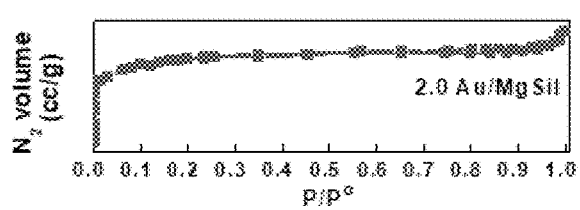
Figure 6A:
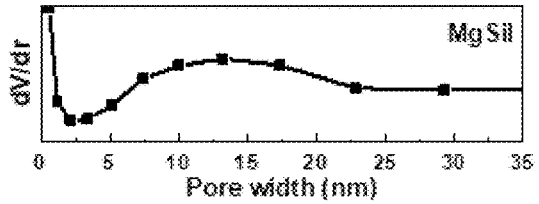
FIGS. 6A-6E show pore size distribution patters for Au/MgSil samples, where
Figure 6B:
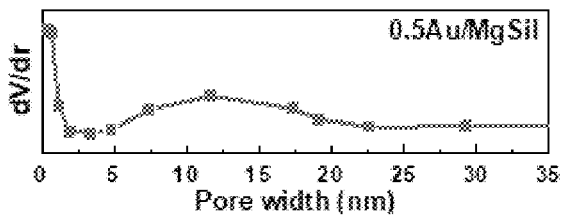
Figure 6C:
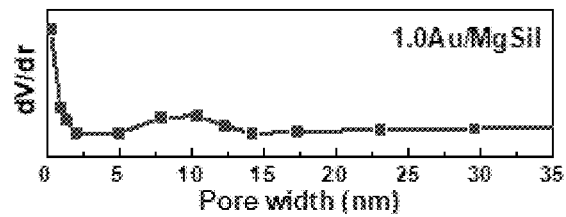
Figure 6D:
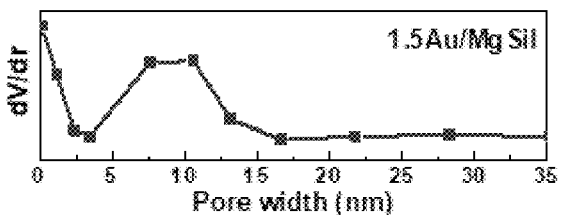
Figure 6E:
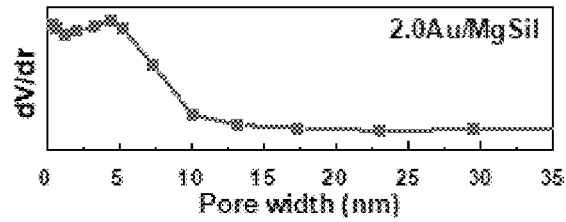

FIG. 4 shows the DR UV-vis spectra of calcined MgSil and Au/MgSil samples. It is clear from the figure that bare MgSil sample exhibited sharp absorption band at 248 nm. It is well known that the UV light absorption beyond 200 nm is due to electronic inter band transitions [B. Balamurugan, T. Maruyama, Appl. Phys. Lett. 87 (2005) 143105]. This behavior is typical for pure magnesium silicates, since no absorbing elements (typically transition or noble metals) with electronic transitions in the visible region are contained. As anticipated, the UV-vis spectra of Au/MgSil samples showed surface plasmon resonance (SPR) band at 525 nm. It is known that the combined excitation of free electrons of the gold nanoparticles normally appears at 520 nm [B. Balamurugan, T. Maruyama, Appl. Phys. Lett. 87 (2005) 143105]. The 5 nm shift in the position of SPR band was detected for all Au/MgSil samples, which could be due to interaction of gold nanoparticles with magnesium silicate framework. It is clear that the intensity of the SPR band increased with increase of gold loading and the shift in band position is observed for all samples. This result is suggesting that gold nanoparticles are not accumulated in the magnesium silicate matrix and also their size was not changed with change in gold loading. The similarity of the absorption spectra of Au/MgSil samples revealing that the gold nanoparticles dispersion is sustained in all the samples and these results are in accordance with FE-SEM results.

The textural characteristics of synthesized Au/MgSil materials were investigated using N$_2$-physisorption measurements. The N$_2$ adsorption-desorption isotherms of the samples are shown in FIG. 5. All the patterns suggests that the synthesized MgSil and Au/MgSil samples exhibits the type IV isotherms with type III hysteresis loop (as per IUPAC classification) at P/P° in the range of 0.45-0.85 due to the presence of large size pores. It is known that it would be hard to measure the micro porosity in case of the materials which possessed type IV isotherms. In case of Au/MgSil samples, the size of the hysteresis loop width was decreased, while the adsorption at low P/P° value (0.2) with a plateau suggesting the decrease in the size of the pores. The pore size distribution patterns were obtained by applying the NLDFT method are presented in FIG. 6. The obtained patterns reveals the presence of macro size pores in the MgSil sample with a wide distribution in the range of 5-20 nm, which are generated due to the structural arrangement of silicate layers. However, when the gold loading is increased to 1.0 wt. % and 2.0 wt. %, the pore size was decreased in the range of 5-10 nm and 2-10 nm respectively.

The obtained results indicating that the amount of gold influences the textural properties of magnesium silicate sample (Table 2). The bare MgSil possessed the surface area, pore volume and pore width of 475 $m^2g^{-1}$, 0.332 $ccg^{-1}$ and 15 nm respectively. Deposition of 2.0 wt. % gold nanoparticles results decrease of surface area, pore volume and pore size width to 338 $m^2g^{-1}$, 0.262 $ccg^{-1}$ and 5.2 nm respectively. The quantitative determination of active Au metal sites on the surface of catalysts was obtained from CO pulse chemisorption experiments. The CO pulses in helium gas were introduced into the U-shaped quartz tube, which loaded with known amount of pretreated catalyst. The Au dispersion was calculated using the quantity of CO consumed and supposing the ratio of CO molecule to Au is equal to 1. The results obtained from CO chemisorption measurements are presented in Table 2. It is clear that the 1.5Au/MgSil catalyst reduced at 250° C. exhibited the highest Au dispersion (59%) among the synthesized Au/MgSil materials because of homogeneous distribution of Au metal nanoparticles over MgSil framework. The availability of Si—OH or Mg—OH functional groups could influence the Au dispersion, as more amount of OH groups on the surface could be a responsible factor for high Au dispersion observed in case of 1.5Au/MgSil catalyst.

TABLE 2

Data obtained from $N_2$ physisorption and CO chemisorption measurements of the samples

| Catalyst | $N_2$ phsisorption | | | CO chemisorption | |
|---|---|---|---|---|---|
| | $S_{BET}$ ($m^2g^{-1}$) | Pore volume ($ccg^{-1}$) | Pore width (nm) | Active sites (molecule CO × $10^{-18}$/ g · cat) | Au dispersion (%) |
| MgSil | 475 | 0.332 | 15.0 | — | — |
| 0.5 Au/MgSil | 421 | 0.321 | 13.5 | 6.82 | 32 |
| 1.0 Au/MgSil | 382 | 0.313 | 11.3 | 8.18 | 47 |
| 1.5 Au/MgSil | 360 | 0.301 | 10.1 | 9.79 | 59 |
| 2.0 Au/MgSil | 338 | 0.262 | 5.2 | 8.02 | 53 |

The XPS analysis was utilized to investigate the surface chemical states and composition of Mg, Si, Au and O species in the MgSil and Au/MgSil materials. The deconvoluted Si2p, Mg2p, Au4f and O1s XPS peaks are shown in FIGS. 7A-7K (representative samples). A single and broad Mg2p XPS peak at binding energy of 50.8 eV was observed for bare MgSil sample. Fotea, e.t al. reported that Mg2p peak at 49.2 eV for metallic Mg species, while the peak at 50.1 eV was assigned to $Mg^{2+}$ in MgO, and the peak at 50.5 eV was attributed to the Mg—O/OH species [C. Fotea, J. Callaway, M. R. Alexander, Surf. Interface Anal. 38 (2006) 1578-1587]. The peak at higher binding energy (approximately 51.4 eV) was associated to crystalline Mg—OH species [V. Rheinheimer, C. Unluer, J. Liu, S. Ruan, J. Pan, P. J. M. Monteiro, Materials, 10 (2017) 75]. In this context, the observed Mg2p peak at 50.8 eV in MgSil sample could be assigned to Mg—O/OH species in magnesium silicate structure. It is interesting to note that all the Au/MgSil samples yielded two Mg2p components (a major one at 49.2 eV and the minor is at 50.2 eV). The major Mg2p peak could be assigned to surface Mg—O—Au metallic species, while the minor peak is due to the $Mg^{2+}$ species in the Au/MgSil samples.

The bulk MgSil sample clearly exhibited a broad Si 2p peak at 103.4 eV. Karmouch, et. al. assigned Si2p peaks at 103.6 eV and 102 eV to Si atoms of siloxane groups (Si—O—Si) and SiO species, respectively [R. Karmouch, G. G. Ross, Appl. Surf Sci. 257(3) (2010) 665-669]. Therefore, the Si 2p peak observed in MgSil sample could be attributed to Si—O—Si in the partially crystalline magnesium silicate framework. The Au/MgSil samples exhibited two deconvoluted Si2p peaks, the most intense at 102.1 eV, which could be due to the Si—O—Au species and a minor peak appear at 99.8 eV could be assigned to the characteristic binding energy of elemental Si [G. F. Cerofolini, C. Galati, L. Renna, Sur. Inter. Anal. 35 (2003) 968-973].

Figure 7A:
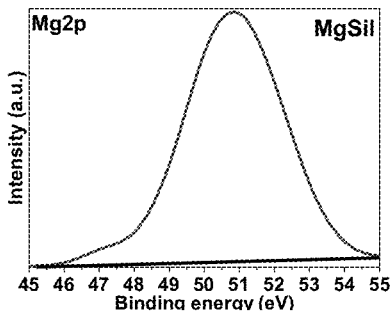
FIGS. 7A-7K are deconvoluted X-ray photoelectron spectroscopy (XPS) spectra for Au/MgSil samples, where
Figure 7B:
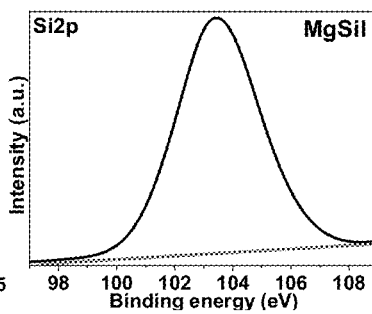
Figure 7C:
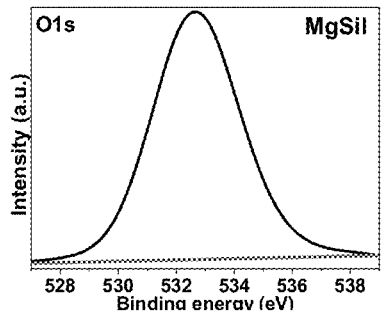
Figure 7D:
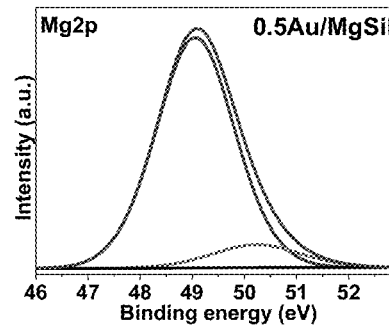
Figure 7E:
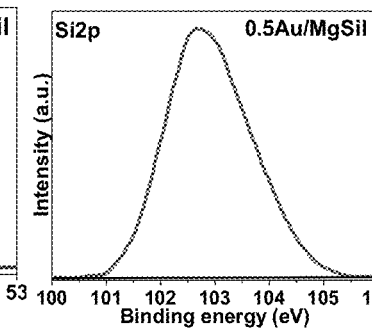
Figure 7F:
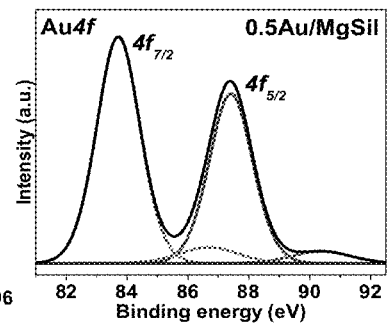
Figure 7G:
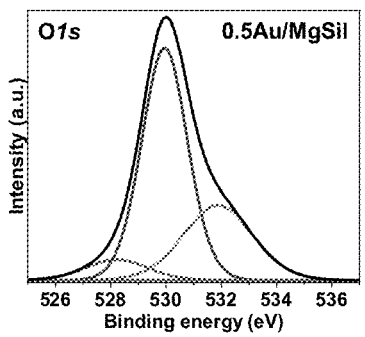
Figure 7H:
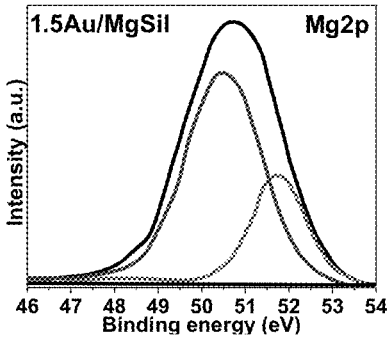
Figure 7I:
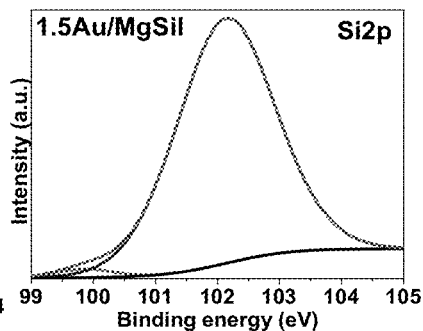
Figure 7J:
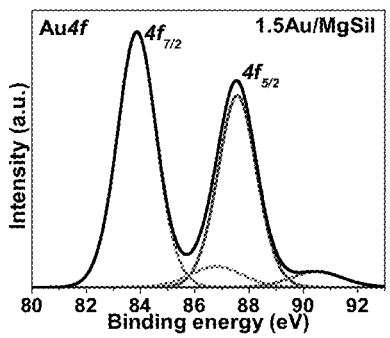
Figure 7K:
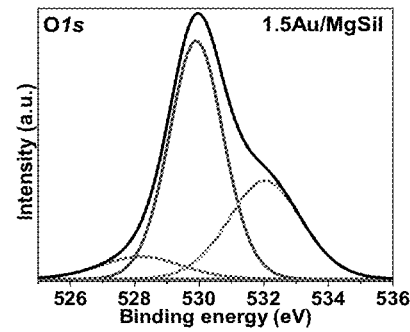
Figure 8A:
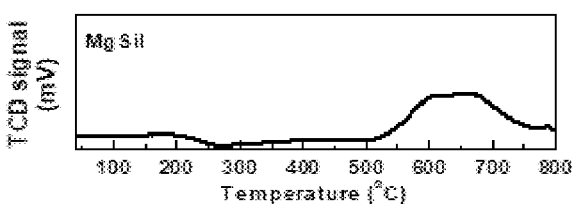
FIGS. 8A-8E show H$_2$-TPR patterns for Au/MgSil catalysts, where
Figure 8B:
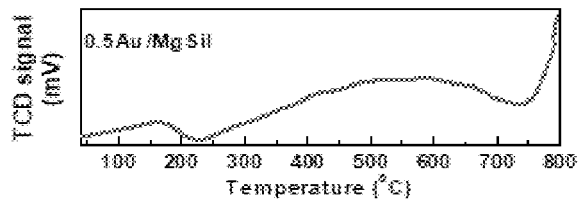
Figure 8C:
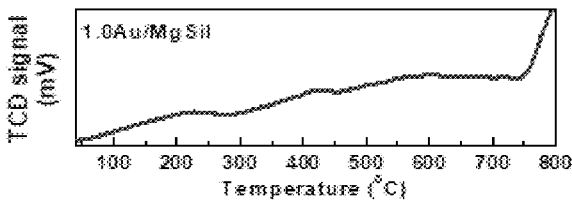
Figure 8D:
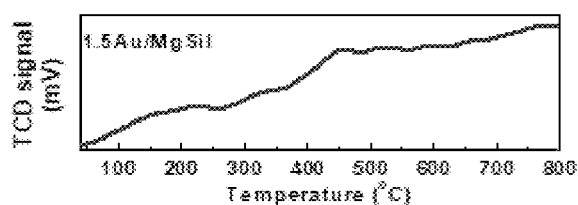
Figure 8E:
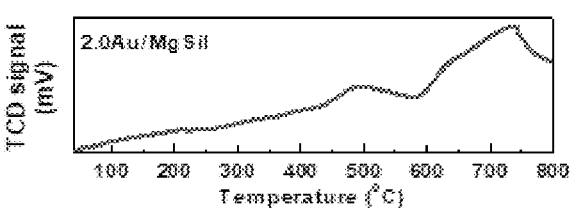
Figure 9A:
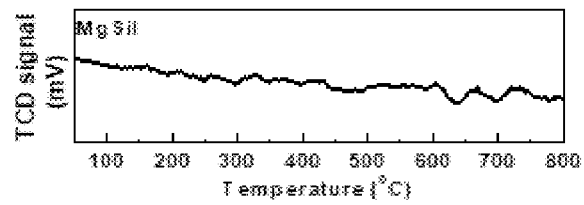
FIGS. 9A-9E show O$_2$-TPD patterns for Au/MgSil catalysts, where
Figure 9B:
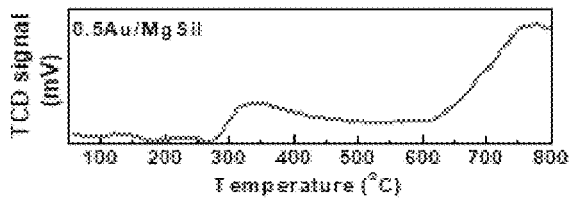
Figure 9C:
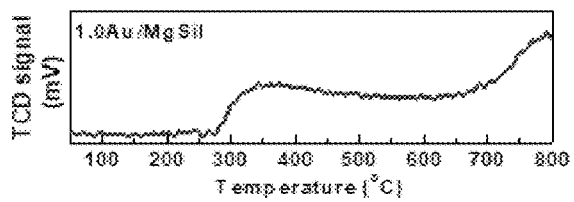
Figure 9D:
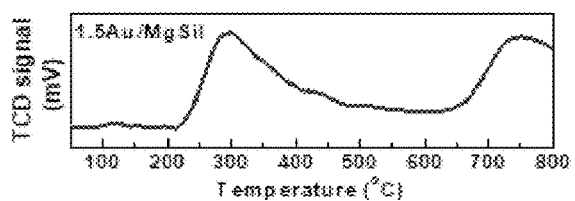
Figure 9E:
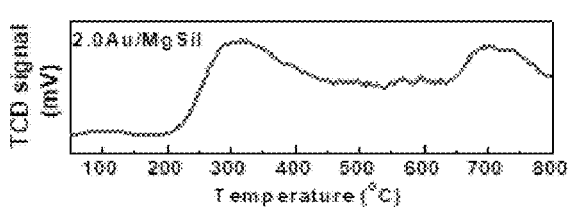
Figure 10A:
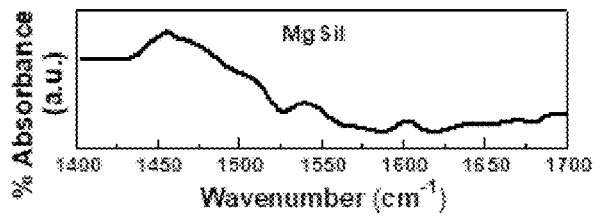
FIGS. 10A-10E show FT-IR spectra of pyridine adsorbed samples for acidity measurements, where
Figure 10B:
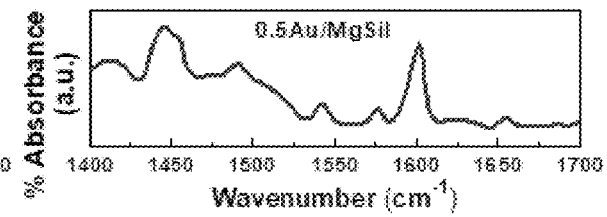
Figure 10C:
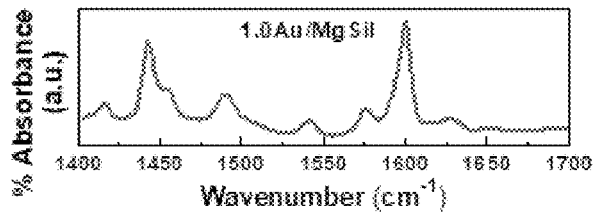
Figure 10D:
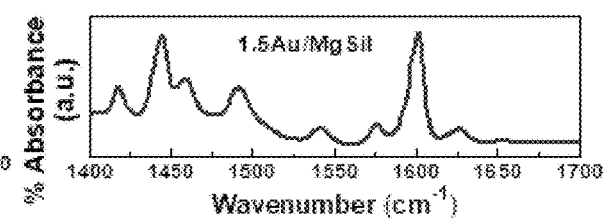
Figure 10E:
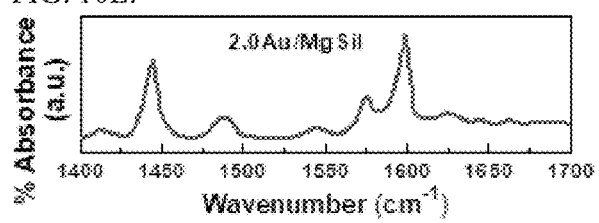

The deconvoluted $Au4f_{7/2}$ and $4f_{5/2}$ peaks for representative samples are also shown in FIGS. 7F and 7J. It is known that $Au4f_{7/2}$ peak for $Au^+$ and $Au^0$ species generally appears at 84.9 eV and 84.0 eV [M. P. Casaletto, A. Longo, A. Martorana, A. Prestianni, A. M. Venezia, Sur. Inter. Anal. 38 (2006) 215-218]. The gold decorated MgSil samples exhibited $Au4f_{7/2}$ and $Au4f_{5/2}$ with binding energy of 83.8 eV and 87.4 eV, which could be assigned for bulk $Au^0$ species revealing that the samples possessed more amount of isolated surface $Au^0$ species. Interestingly, the samples also showed minor $Au4f_{7/2}$ and $4f_{5/2}$ peaks at higher binding energies (86.5 eV and 90.5 eV), which could be assigned to bulky (possibly the Au—O—Si/Mg) species [W. Y. Hemindez, F. Aliç, S. Navarro-Jaen, M. A. Centeno, P. Vermeir, P. Van Der Voort, A. Verberckmoes, J. Mater. Sci. 52 (2017) 4727-4741]. The XPS analysis results clearly indicating that there is a clear interaction existed between the Au nanoparticles and surface of MgSil support. The MgSil sample exhibited single broad O1s peak at 532.5 eV, which is in good agreement with O1s binding energy position of MgSil reported in the literature (normally appears between binding energies of 533.3 eV ($SiO_2$) and 531.8 eV (MgO)). However, the gold decorated MgSil samples showed three O1s XP peaks at 528.3 eV, 530.1 eV and 532.2 eV. The peak observed at 528.3 eV could be attributed to adsorbed O atoms on $Au^0$ species [T. E. Jones, T. C. R. Rocha, A. Knop-Gericke, C. Stampfl, R. Schlogl Simone Piccinin, Phys. Chem. Chem. Phys. 17 (2015) 9288]. The major peak at 530.1 eV is due to the lattice oxygen in the magnesium silicate network and the third peak at 532.2 eV could be attributed oxygen in the Au—O—Mg/Si (interactive) species.

TABLE 3

Elemental composition determined from ICP-AES and XPS analyses of the samples

| Catalyst | ICP-AES (mass %) | | | | XPS (mass %) | | | |
|---|---|---|---|---|---|---|---|---|
| | Mg | Si | O | Au | Mg | Si | O | Au |
| MgSil | 34.1 | 11.6 | 54.3 | — | 34.1 | 11.5 | 54.3 | — |
| 0.5 Au/MgSil | 33.7 | 11.4 | 54.0 | 0.45 | 33.7 | 11.4 | 54.0 | 0.44 |
| 1.0 Au/MgSil | 33.3 | 11.2 | 53.8 | 0.96 | 33.3 | 11.2 | 53.7 | 0.94 |
| 1.5 Au/MgSil | 33.1 | 11.1 | 53.6 | 1.45 | 33.1 | 11.1 | 53.6 | 1.43 |
| 2.0 Au/MgSil | 32.9 | 11.0 | 53.3 | 1.97 | 32.9 | 11.0 | 53.3 | 1.93 |

The bulk chemical composition of the synthesized Au/MgSil materials was determined using ICP-AES technique. It is clear from the results that composition of MgSil sample is corresponding to formula of 3MgO.4SiO$_2$ as the total atomic ratio of Mg to Si is about 3:4. All the gold decorated MgSil samples also possessed similar bulk chemical composition, while the determined surface Mg:Al ratios and Au composition were slightly decreased, probably due to the formation of surface interactive species between the gold and MgSil support.

The reducibility of the synthesized MgSil and Au/MgSil samples are studied using H$_2$-TPR analysis (see FIG. 8). The H$_2$-TPR pattern of bulk MgSil sample showed a minor reduction peak in the low temperature region at 120-250° C. is because of reduction of OH-groups on the surface of magnesium silicate [S. Cimino, L. Lisi, M. Tortorelli, Chem. Eng. J. 283 (2016) 223-230]. The two broad reduction peaks in the region of 500-760° C. It is well known that normally reduction of MgO and SiO$_2$ does not occur below 800° C., therefore the two peaks could be attributed to the reduction of Mg—O—Si species at two different sites [J. Leszczyński, A. Mizera, J. Nieroda, P. Nieroda, E. Drozdz, M. Sitarz, A. Koleżyński, J. Therm. Anal. Calor. 140 (2020) 2657-2666]. A shift in the low temperature and high temperature reduction peaks was observed in the H$_2$-TPR patterns of Au/MgSil samples. The existence of more number of reactive oxygen species and their localization in the Au-MgSil interface could be the reason for the shift in reduction temperature. The Au/MgSil samples also showed incomplete reduction peaks at high temperatures (above 760° C.). A similar observation was reported in case of NiO incorporated MgSil catalysts as NiO interacted with MgO and SiO$_2$ were reduced above 700-900° C. [F. Barzegari, M. Kazemeini, F. Farhadi, M. Rezaei, A. Keshavarz, Inter. J. Hyd. Energy, 45 (2020) 6604-6620]. Therefore, the incomplete reduction peak at higher temperature is probably related to the strongly interacted Au—O—Mg/Si species, while the lower temperature peaks could be attributed to the gold oxide species on the magnesium silicate surface with a weaker interaction. The H$_2$-TPR analysis clearly indicated that the reduction peaks shifted to lower temperature with higher gold loading, which indicates that more readily reducible gold species were favored to form by increasing the gold loading.

FIG. 9 shows the O$_2$-TPD patterns of the synthesized samples. The bulk MgSil sample not shown any O$_2$ desorption peaks below 800° C., due to the fact that magnesium silicate have not possessed any surface oxygen containing (O$^{2-}$, O$^-$) or liable lattice oxygen species. Deposition of gold nanoparticles over the surface MgSil resulted a drastic change in the O$_2$ desorption ability; two O$_2$ desorption peaks were observed in all the Au/MgSil samples. One peak at low temperature (300-350° C.) and another at high temperature (above 700° C.). It is well known that the chemisorbed oxygen species could easily desorb at low temperature, however lattice oxygen species requires high temperatures to desorb [K. Tamai, S. Hosokawa, K. Kato, H. Asakura, K. Teramura, T. Tanaka, Phys. Chem. Chem. Phys. 22 (2020) 24181-24190]. The desorption peaks observed at low temperature in TPD patterns of Au/MgSil samples could be attributed to surface oxygen species weakly bonded with decorated Au nanoparticles. The O$_2$ desorption peaks at high temperature are associated with the desorption of lattice oxygen from the interactive species (Au—O—Mg/Si), as O$_2$-TPD pattern of bulk MgSil sample have not shown peaks at low or high temperature regions. It is also clear from the TPD patterns that intensity of desorption peak at low temperature was increased with increase of gold loading, while the intensity of high temperature peak was decreased. This observation is revealing the interaction between the gold and MgSil decreasing with increase of gold loading and balance between isolated gold and interactive gold species were achieved in case of 1.5Au/MgSil sample. The quantification of these two species was performed and the results are presented in Table 4.

TABEL 4

Data obtained from H2-TPR, O2-TPD and acidity measurements of the samples

| Catalyst | H$_2$-TPR (μ moles g$^{-1}$) | O$_2$-TPD (μ moles g$^{-1}$) | Number of acid sites Lewis (L) | Bronsted (B) |
|---|---|---|---|---|
| MgSil | 158.4 | — | 1.1 | — |
| 0.5 Au/MgSil | 1325.5 | 42.6 | 10.2 | 0.35 |
| 1.0 Au/MgSil | 1687.4 | 58.8 | 16.5 | 0.43 |
| 1.5 Au/MgSil | 2054.1 | 73.2 | 23.3 | 0.68 |
| 2.0 Au/MgSil | 1845.8 | 63.7 | 20.7 | 0.53 |

It was previously observed that oxidative cracking ability of the catalysts influenced by the acidic and basic properties of the total catalysts, therefore acidity of the catalysts was investigated by measuring FT-IR spectra of pyridine adsorbed samples. The obtained spectra of the MgSil and Au/MgSil catalysts are presented in FIG. 10. The bulk MgSil sample have not possessed presence of appreciable number of Lewis or Brønsted acid sites, as the FT-IR spectrum showed minor intense peaks. It is clear that FT-IR spectra of pyridine adsorbed Au/MgSil samples exhibited a major sharp peak at 1445 cm$^{-1}$ which could be ascribed to pyridine molecule bonded to Lewis acid sites and appearance of minor peak at 1545 cm$^{-1}$, which is corresponding to Brønsted acid sites confirms that the presence of isolated Au$^0$ and interactive Au—O—Mg/Si species responsible for generated Lewis acid sites [B. Al-Shammari, Q. Alsulami, K. Narasimharao, Catalysts, 9 (2019) 979]. The quantification of acid sites was accomplished and the results were presented in Table 4. Among all the synthesized samples in this study, 1.5Au/MgSil sample possessed more number of Lewis acid sites.

Figure 11A:
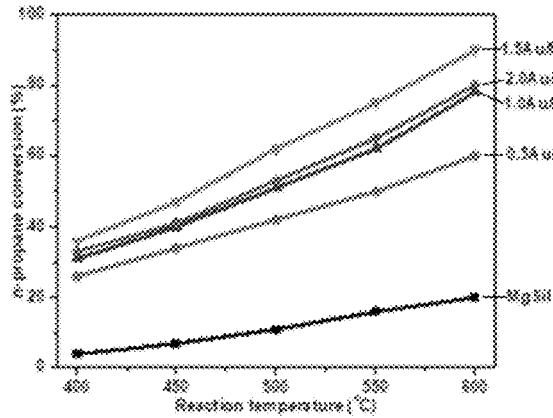
FIGS. 11A-11B are plots of n-propane conversion and olefins selectivity over MgSil and Au/MgSil catalysts at different reaction temperatures (GHSV=48,000 h$^{-1}$), where

Catalytic activity of synthesized bulk MgSil and Au/MgSil samples for catalytic oxidative cracking of n-propane was studied using quartz micro-reactor at different reaction conditions. The major reaction products observed in the oxidative cracking of n-propane over Au/MgSil catalysts have been C$_3$H$_6$, C$_2$H$_4$ and CO$_2$. Low concentrations of CO, CH$_4$ and C$_2$H$_6$ were identified. The n-propane conversions at different reaction temperatures (in the range of 400-600° C.) for MgSil and Au/MgSil catalysts are presented in FIG. 11A. As shown in the figure, the bare MgSil sample shows considerable catalytic oxidative cracking activity at high reaction temperature. The conversion of n-propane reached to 20% at 600° C. In contrast, MgSil catalysts with gold nanoparticles exhibited significant n-propane conversion in the investigated reaction temperature range. The rate of n-propane conversion and selectivity to light olefins (ethylene and propylene) increased exponentially with temperature. The highest n-propane conversion was observed in case of 1.5Au/MgSil (90%) at 600° C. Addition of more amount of gold to the MgSil support led to decrease in catalytic activity (80%) for 2.0Au/MgSil catalyst.

Figure 11B:
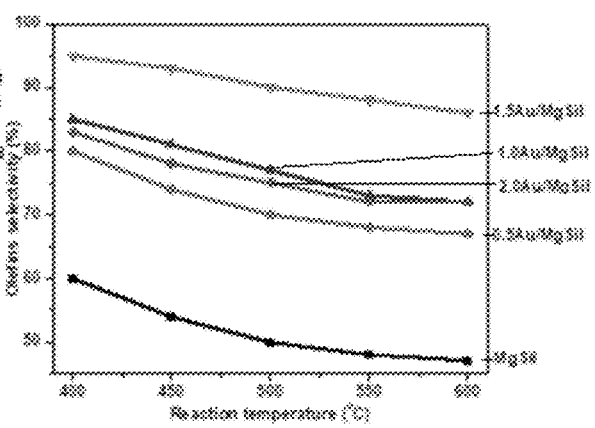

It is clear that the high olefins (ethylene and propylene) selectivity was observed at low reaction temperature in case of all the investigated catalysts. The olefins selectivity was first decreased with increase of reaction temperature, however it was almost constant at higher reaction temperatures (550° C. and 600° C.) (See FIG. 11B). The highest olefin selectivity values were 95%, 82% and 65% for 1.5Au/ MgSil, 2.0Au/MgSil and MgSil catalysts respectively. For bare MgSil catalyst, the selectivity to olefins decreased from 65% to 55%, while the selectivities to CO and $CO_2$ increased with increase of reaction temperature (600° C.). In case of 1.5Au/MgSil catalyst, the olefins selectivity also changed slightly (86%), due to the formation of CO and $CO_2$ at 600° C. Table 5 presents n-propane conversion and different products formed during oxidative cracking data over the bulk MgO, $SiO_2$, MgSil and Au/MgSil catalysts at 600° C. and GHSV=48,000 $h^{-1}$. The bulk $SiO_2$ and MgO materials were also tested to compare their oxidative cracking activities with MgSil and Au/MgSil catalysts. The bulk $SiO_2$ and MgO catalysts exhibited low n-propane conversions and olefins selectivities at investigated reaction conditions. It is clear that gold supported MgSil catalysts offered superior oxidative cracking catalytic activity compared to bulk MgSil, MgO and $SiO_2$ because Au/MgSil catalysts possessed more number of Lewis acid sites and liable oxygen species. It is also interesting to note that at 600° C., formation of minor quantities of methane and ethane were observed in case of all the investigated catalysts (see Table 5).

TABLE 5

Oxidative cracking of n-propane over MgO, $SiO_2$, MgSil and Au/MgSil catalysts at 600° C. and GHSV = 48,000 $h^{-1}$

| Catalyst | Con. n-propane (%) | Selectivity of products (%) | | | |
|---|---|---|---|---|---|
| | | Olefins | $CH_4$ | $C_2H_6$ | $CO_x$ |
| MgSil | 20 | 47 | 2.3 | 5.5 | 45.2 |
| 0.5 Au/MgSil | 60 | 67 | 1.1 | 1.4 | 30.5 |
| 1.0 Au/MgSil | 78 | 72 | 0.8 | 1.2 | 26.0 |
| 1.5 Au/MgSil | 90 | 86 | 0.7 | 0.9 | 12.4 |
| 2.0 Au/MgSil | 80 | 73 | 1.2 | 1.4 | 24.4 |
| $SiO_2$ | 4 | 20 | 0.5 | 1.5 | 78.0 |
| MgO | 13 | 40 | 1.7 | 5.0 | 53.3 |

Figure 12A:
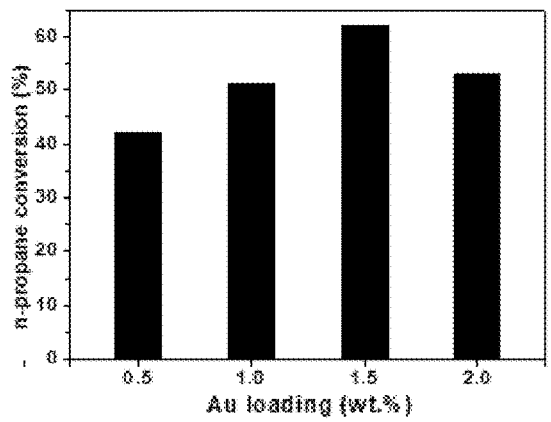
FIGS. 12A-12B are bar graphs depicting the influence of gold loading over conversion of n-propane and selectivity to olefins for reaction temperature 500° C. and GHSV=48,000 h$^{-1}$, where
Figure 12B:
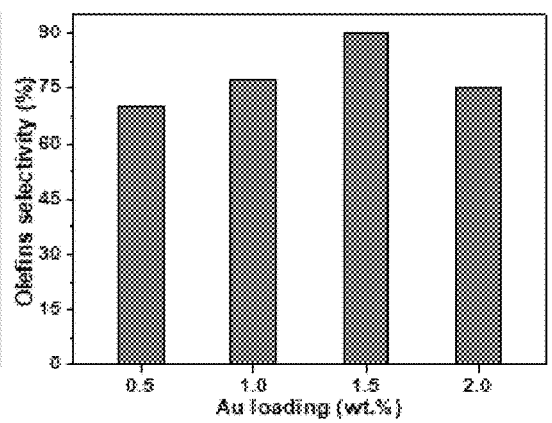

The obtained data revealed that conversion of n-propane and selectivity to olefins were enhanced afterwards decoration of Au species (0.5 to 1.5 wt. %) over MgSil support (see FIGS. 12A-12B). These observations are indicating that presence of interactive Au species on the surface of MgSil played a crucial role for improvement in oxidative cracking ability of the catalysts. A strong interaction between the Au species and MgSil support could lead to existence of a synergetic effect, which is responsible for enhancement in the catalytic oxidative cracking performance. Increase of Au loading further to 2.0 wt. % caused fall in both conversion and selectivity levels. This is possibly because of agglomeration of Au nanoparticles on the surface of MgSil support hindering the accessibility of active Au-MgSil interactive species to n-propane molecules.

Figure 13A:
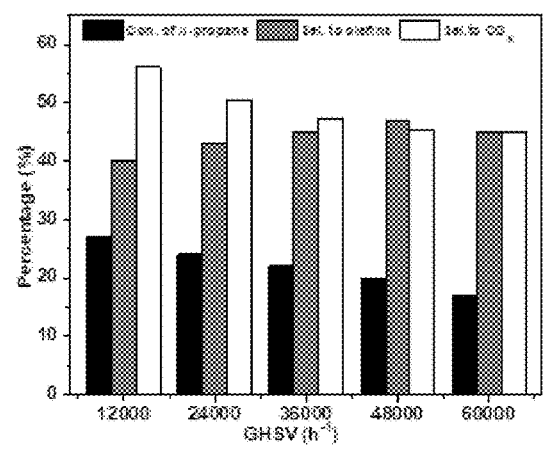
FIGS. 13A-13B are bar graphs depicting the influence of GHSV conversion of n-propane, selectivity to olefins and selectivity to CO, for MgSil and 1.5Au/MgSil catalysts at reaction temperatures of 600° C., where
Figure 13B:
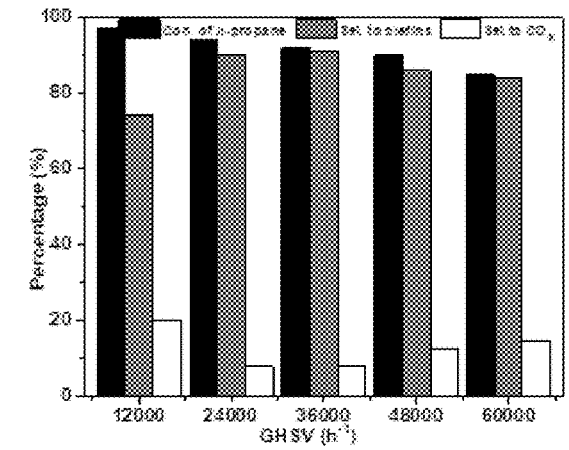

Conversion of n-propane, olefins selectivity and COX selectivity levels were obtained by using various GHSV values at 600° C. for all the synthesized Au/MgSil catalysts, The influence of GHSV on oxidative cracking activity of MgSil and 1.5 Au/MgSil catalysts are presented in FIGS. 13A-13B. It is observed that both catalysts exhibited relatively high n-propane conversions and low olefins selectivity at low GHSV value (12000 $h^{-1}$); majorly due to the olefins decomposition over the catalyst surface as the low GHSV lead to more residence time. Slight decrease in n-propane conversion was perceived with increase of GHSV, however, increase in selectivity olefins was observed. Interestingly, further increase of GHSV to 60000 $h^{-1}$ resulted decrease of n-propane conversion and without further increase of olefins selectivity, therefore it is reasonable to argue that optimum n-propane conversion with high olefins selectivity were obtained at GHSV of 48000 $h^{-1}$.

Figure 14A:
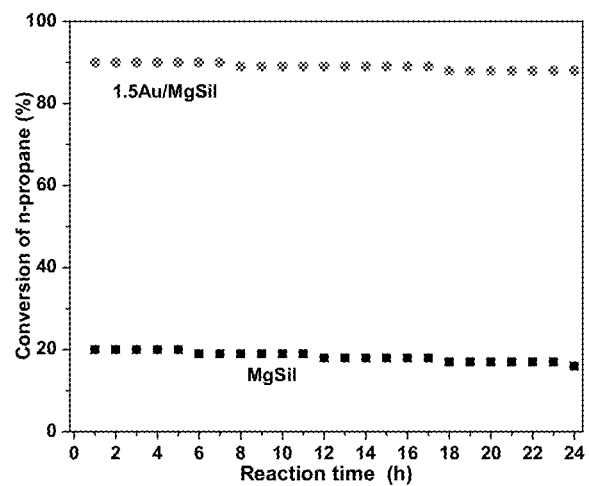
FIGS. 14A-14B are plots depicting time on stream analysis of MgSil and 1.5Au/MgSil catalysts at reaction temperature of 600° C. and GHSV=48,000 h$^{-1}$ where
Figure 14B:
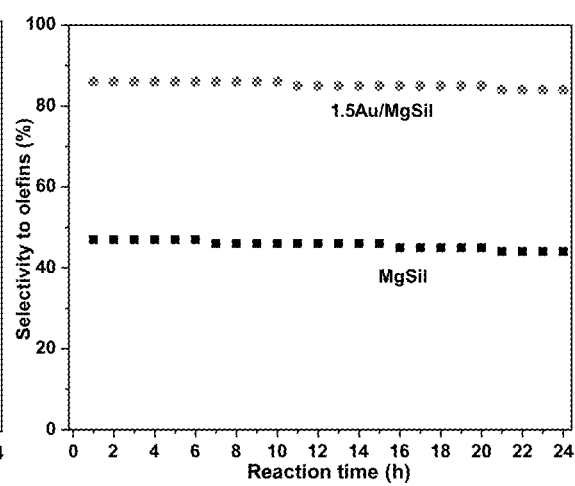

To test the durability of synthesized MgSil support and Au/MgSil samples, catalytic oxidative cracking of n-propane was carried out at 600° C. over MgSil and 1.5Au/MgSil catalysts for 24 h. The n-propane conversion and selectivity of olefins levels obtained over MgSil and 1.5Au/MgSil samples are presented in FIGS. 14A-14B. The results from the durability tests revealed that MgSil and 1.5Au/MgSil catalysts showed stable n-propane conversion and olefins selectivity at 600° C. for 24 hours. A slight decrease in performance could be due to agglomeration of MgSil and gold particles, however considerable decline in conversion of n-propane and olefins selectivity were not witnessed for prolong hours of operation.

The characterization results of Au/MgSil catalysts are used to understand and correlate the physico-chemical properties of the catalysts with their oxidative cracking performance. The bulk MgSil, MgO and $SiO_2$ materials exhibited low n-propane conversion levels, since activation of C—H bond in n-propane is the rate-determining step in these materials [N. M. Phadke, E. Mansoor, M. Bondil, M. Head-Gordon, A. T. Bell, J. Am. Chem. Soc. 141 (2019) 1614-1627]. In case of bulk MgSil, MgO and $SiO_2$ materials, the C—H bond activation is catalyzed by either acid or acid-base sites, which are existed on surface of synthesized MgSil samples[D. Schroder, J. Roithovi, E. Alikhani, K. Kwapien, J. Sauer, Chemistry 16 (2010) 4110-4119]. However, the acid-base sites presented in bulk MgSil sample are not efficient; minor quantities of products from oxidative cracking were noticed. Decoration of gold nanoparticles on the surface of MgSil material resulted major growth in the n-propane conversion and olefins selectivity. The decorated gold species on the surface of MgSil support are highly active for n-propane dehydrogenation. The gold species in the active Au/MgSil catalysts are majorly metallic nanoparticles, as evidenced by XRD and DR UV-vis spectroscopy. The gold species catalyze the C—H bond activation efficiently and also recombination and desorption of $H_2$ molecules is faster in case of gold species compared to acid-base sites [F. Ma, Q-Y. Chang, Q. Yin, Z-J. Sui, X-G. Zhou, D. Chen, Y-A. Zhu, Catal. Sci. Technol., 10, (2020) 4938-4951]. The conversion of n-propane and olefins selectivity increased with increase of gold loading until 1.5 wt. % and further increase of gold loadings did not result in higher conversions; thus, 1.5 wt. % loading could be considered as an optimum. The decrease in oxidative cracking ability in high gold loading catalysts could be due to decrease of gold dispersion; due to the formation of large size gold nanoparticles in these catalysts as observed in the XRD results.

The acid characteristics of Au/MgSil catalysts can have an important influence on the adsorption and desorption of reactants and products, and therefore on the catalytic performance. Thus, it is possible to correlate the olefins selectivity with the acid characteristics of the catalysts, considering the results achieved by FT-IR spectra of samples after pyridine adsorption. The obtained results clearly indicated that the higher the amount and strength of Lewis acid sites on Au/MgSil catalysts, the higher the selectivity to olefins during the oxidative cracking of n-propane and among the synthesized samples 1.5Au/MgSil catalyst have high quantity of Lewis acid sites. It was previously observed that [$Au^+O^-$] acts as active site for C—H activation and olefins known to be less reactive compared to alkanes with oxygen over the basic oxide-based catalyst [W. Panjana, J. Sirijaraensrea, C. Warakulwita, P. Pantua, J. Limtrakul, Phys. Chem. Chem. Phys., 14 (2012) 16588-16594]. The catalyst performance for oxidative cracking process is influenced by the oxygen supplying capability of the catalyst active surface. During the oxidative cracking process, the alkane molecule is continually oxidized by the oxygen molecule. The continual supply of oxygen species facilitates the proceeding of the reaction. It was reported that desorption peak area and temperature maximum of desorption peaks of $O_2$-TPD desorption patterns provides the information related to the quantity of oxygen supplying centers [C. T. Campbell, J. C. Sharp, Y. X. Yao, Eric M. Karp, T. L. Silbaugh, Faraday Discuss. 152 (2011) 227-239]. In case Au/MgSil catalysts, low temperature $O_2$ desorption peak was appeared due to gold deposition. The oxygen species chemisorbed at different temperatures could supply active oxygen species during the reaction. The amount of liable oxygen species was increased with increase of gold loading up to 1.5 wt. % and more liable oxygen species offer an effective way to achieve lower reaction temperature. The addition of optimum amount of gold nanoparticles altered the surface environment of MgSil and improves the storage of active oxygen species in supported Au/MgSil catalysts, providing further evidence for superior performance of synthesized Au/MgSil catalysts.

The invention claimed is:

1. A nanomaterial catalyst, comprising:
    a partially crystalline porous magnesium silicate support which is substantially free of titanium and aluminum; and
    gold nanoparticles dispersed on the partially crystalline porous magnesium silicate support, wherein the gold nanoparticles are present in an amount of 0.5 to 1.5 wt. %, based on a total weight of nanomaterial catalyst and have an average particle size of from 18 to 22 nm,
    wherein the nanomaterial catalyst is substantially free of Group VIII metals.

2. The nanomaterial catalyst of claim 1, wherein the partially crystalline porous magnesium silicate support has a Mg to Si molar ratio of 1:1 to 5:1.

3. The nanomaterial catalyst of claim 1, wherein the partially crystalline porous magnesium silicate support has a single crystalline phase by powder X-ray diffraction.

4. The nanomaterial catalyst of claim 1, wherein the partially crystalline porous magnesium silicate support has an average crystallite size of 5 to 50 nm by powder X-ray diffraction.

5. The nanomaterial catalyst of claim 1, which has a surface area of 300 to 500 $m^2/g$ and a pore volume of 0.225 to 0.375 $cm^3/g$.

6. The nanomaterial catalyst of claim 1, which has an acidity of 7.5 to 30 mmol/g.

7. The nanomaterial catalyst of claim 1, wherein the nanomaterial catalyst consists of:
    the partially crystalline porous magnesium silicate support having a Mg to Si molar ratio of 1:1 to 5:1; and
    the gold nanoparticles,
    wherein the nanomaterial catalyst has a surface area of 300 to 500 $m^2/g$, a pore volume of 0.225 to 0.375 $cm^3/g$, and an acidity of 7.5 to 30 mmol/g.

* * * * *